United States Patent
Seon

(10) Patent No.: US 6,190,660 B1
(45) Date of Patent: *Feb. 20, 2001

(54) ANTI-ENDOGLIN MONOCLONAL ANTIBODIES AND THEIR USE IN ANTIANGIOGENIC THERAPY

(75) Inventor: Ben K. Seon, Williamsville, NY (US)

(73) Assignee: Health Research, Inc., Buffalo, NY (US)

( * ) Notice: Under 35 U.S.C. 154(b), the term of this patent shall be extended for 0 days.

This patent is subject to a terminal disclaimer.

(21) Appl. No.: 09/497,833

(22) Filed: Feb. 3, 2000

Related U.S. Application Data

(60) Continuation-in-part of application No. 09/312,382, filed on May 14, 1999, which is a division of application No. 08/920,537, filed on Aug. 29, 1997, now Pat. No. 5,928,641, which is a continuation-in-part of application No. 08/655,953, filed on May 31, 1996, now abandoned.

(51) Int. Cl.$^7$ ........................ A61K 39/395; A61K 39/40; A61K 39/42; C07K 1/00; C07K 14/00
(52) U.S. Cl. ..................... 424/130.1; 424/133.1; 424/141.1; 424/142.1; 530/350
(58) Field of Search ............... 424/130.1, 133.1, 424/141.1, 142.1; 530/350

(56) References Cited

U.S. PATENT DOCUMENTS

| | | | |
|---|---|---|---|
| 5,407,805 | 4/1995 | Seon | 435/7.23 |
| 5,776,427 | 7/1998 | Thorpe et al. | 424/1.49 |

OTHER PUBLICATIONS

Austyn et al., "Principles of Cellular and Molecular Immunology," pp. 37 and 38 (1979).
Pharmingen Biological Reagents Catalog, p. 43 (1968).
Sevier et al., "Monoclonal Antibodies in Clinical Immunology," Clinical Chemistry, vol. 27, No. 11, 1981, pp. 1797–1806.
St. Jacques et al., "Molecular Characterization and in Situ Localization of Murine Endoglin Reveal that it is a Transforming Growth Factor–β Binding Protein of Endothelial and Stromal Cells," Endocrinology, 1994, pp. 2645–2657.
Better et al., Potent anti–CD5 ricin A chain immunoconjugates from bacterially produced Fab' and F(ab')$_2$, Proc. Natl. Acad, Sci. USA, vol. 90, Jan. 1993, pp. 457–461.
Owens, et al.; "The genetic engineering of monoclonal antibodies," Journal of Immunogical Methods 168, 1994, pp. 149–165.
Ge et al., "Cloning and expression of a cDNA encoding mouse endoglin, and endothelial cell TGF–β ligand," Gene, 1994, pp. 201–206.
Haruta et al., "Distinct human leukemia–associated cell surface glycoprotein GP160 defined by monoclonal antibody SN6," Proc. Natl. Acad. Sci. USA, vol. 83, Oct. 1986, pp. 7898–7902.
Thorpe et al., "Antibody–directed targeting of the vasculature of solid tumors," Breast Cancer Research and Treatment 36, 1995, pp. 237–251.
Burrows, et al, "Up–Regulation of Endoglin on Vascular Endothelial Cells in Human Solid Tumors: Implications for Diagnosis and Therapy", Clin. Can. Res. 1:1623–1634, 1995.
Seon, et al, Monoclonal Antibody that Defines a Unique Human T–cell Leukemia Antigen, PNA's 80:845–849, 1983.

*Primary Examiner*—Jeffrey Stucker
*Assistant Examiner*—Brett Nelson
(74) *Attorney, Agent, or Firm*—Hodgson, Russ, Andrews, Woods & Goodyear LLP

(57) ABSTRACT

A monoclonal antibody, or fragments thereof, having binding specificity for both endoglin expressed on human vascular endothelial cells and on murine endothelial cells. Antiangiogenic therapy in mammals can be effected by administering to the mammalian host a therapeutically effective amount of an anti-endoglin monoclonal antibody, or fragment thereof, either unconjugated or conjugated to at least one angiogenesis inhibitor or antitumor agent. The composition is useful for treating tumor and angiogenesis-associated diseases.

25 Claims, 14 Drawing Sheets

ANTI-ENDOGLIN MONOCLONAL ANTIBODIES AND THEIR USE IN ANTIANGIOGENIC THERAPY

This application is a continuation-in-part of copending U.S. patent application Ser. No. 09/312,382, filed on May 14, 1999, which is a divisional of U.S. patent application Ser. No. 08/920,537, filed on Aug. 29, 1997, now U.S. Pat. No. 5,928,641, which in turn is a continuation-in-part of U.S. patent application Ser. No. 08/655,953, filed May 31, 1996, now abandoned, the disclosures of which are incorporated herein by reference.

This invention was made with government support under grant CA 19304 awarded by the U.S. Public Health Service. The government has certain rights in the invention.

FIELD OF THE INVENTION

The present invention is related to compositions and methods for antiangiogenic therapy of certain disease types in humans. More particularly, the present invention is related to the production of anti-endoglin monoclonal antibodies, and a method for treating cancers and other pathological conditions associated with angiogenesis in humans in conjunction with administration of anti-endoglin monoclonal antibodies, and immunoconjugates comprising anti-endoglin monoclonal antibodies.

BACKGROUND OF THE INVENTION

1. Endoglin

Endoglin is a homodimeric membrane glycoprotein which is expressed at high levels in proliferating vascular endothelial cells (Burrows et al., 1995, *Clin. Cancer Res.* 1:1623–1634). Thus, endoglin is primarily a proliferation-associated marker for endothelial cells undergoing active angiogenesis. However, there is some expression of endoglin by the vascular endothelium of normal tissues (Burrows et al., supra; Wang et al., 1993, *Int. J. Cancer* 54:363–370). Recently, human endoglin was determined to specifically bind transforming growth factor-β (TGF-β), and the deduced amino acid sequence of endoglin showed strong homology to β-glycan, a type of TGF-β receptor.

Murine endoglin has been characterized as a dimer with molecular size of approximately 180 kilodaltons (kD). Human endoglin exists in two forms; i.e., a smaller 160 kD form and a larger 170 kD form with the difference between the two being found in the cytoplasmic portion of the protein. Endoglin has an extracellular region, a hydrophobic transmembrane region, and a cytoplasmic tail. A comparison of the nucleotide sequence of human endoglin with murine endoglin reveals an identity of about 71 to 72% (St. Jacques et al., 1994, *Endocrinol.* 134:2645–2657; Ge et al., 1994, *Gene* 158:2645–2657). However, in the human and murine sequences encoding the transmembrane regions and cytoplasmic regions of endoglin, there is a 93–95% identity. Thus, in the human and murine sequences encoding the extracellular region to which antibody would be directed at the cell surface, there is significantly less identity than 70%. Although the amino acid sequence similarity between human and mouse endoglins appears substantial, the observed amino acid sequence differences in the extracellular regions should be sufficient for generating distinct antigenic epitopes unique to human endoglin or to mouse endoglin. This is because in peptide epitopes, even a subtle variation in the amino acid sequence comprising the epitopes or in the flanking amino acid sequences can markedly influence the immunogenicity of the epitopes (see, e.g., Vijayakrishnan et al., 1997, *J. Immunol.* 159:1809–1819). For instance, single amino acid substitutions in a peptide can cause marked changes in the immunogenicity of the peptide (Vijayakrishnan et al., 1997, supra). Such changes in a peptide epitope will strongly influence the specificity of mAbs because mAbs define fine specificity.

2. Monoclonal Antibodies to Endoglin

There have been several anti-endoglin monoclonal antibodies ("mAb") previously reported in the art. mAb SN6 is an antibody generated from immunization of mice with glycoprotein mixtures of cell membranes of human leukemia cells (Haruta and Seon, 1986, *Proc. Natl. Acad. Sci.* 83:7898–7902). It is a murine mAb that recognizes human endoglin. mAb 44G4 is an antibody generated from immunization of mice with whole cell suspensions of human pre-B leukemia cells (Gougos and Letarte, 1988, *J. Immunol.* 141:1925–1933; 1990, *J. Biol. Chem.* 265:8361–8364). It is a murine mAb that recognizes human endoglin. mAb MJ7/18 is an antibody generated from immunization of rats with inflamed mouse skins (Ge and Butcher, 1994, supra). It is a mAb that recognizes murine endoglin. mAb Tec-11 is an antibody generated from immunization of mice with human umbilical vein endothelial cells (Burrows et al., 1995, *Clin. Cancer Res.* 1:1623–1634). It is a murine mAb with reactivity restricted to human endoglin.

By the use of anti-endoglin antibodies and various staining procedures known in the art, it has been determined that endoglin is expressed at moderate levels on human tumor cells such as from human leukemia, including non-T-cell-type (non-T) acute lymphoblastic leukemia (ALL), myelomonocytic leukemia. In addition, it has been determined that endoglin is expressed at moderate to high levels in endothelial cells contained in tumor-associated vasculatures from human solid tumors, including angiosarcoma, breast carcinoma, cecum carcinoma, colon carcinoma, Hodgkins lymphoma, lymphoma, lung carcinoma, melanoma, osteosarcoma, ovarian carcinoma, parotid tumor, pharyngeal carcinoma, rectosigmoid carcinoma; and human vasculature from placenta, adrenal and lymphoid tissues. A lesser degree (weak) endothelial cell staining for endoglin has been observed in a variety of normal human adult tissue sections from spleen, thymus, kidney, lung and liver.

Increased endoglin expression on vascular endothelial cells has also been reported in pathological conditions involving angiogenesis. Such angiogenesis-associated diseases include most types of human solid tumors, rheumatoid arthritis, stomach ulcers, and chronic inflammatory skin lesions (e.g., psoriasis, dermatitis; Westphal et al., 1993, *J. Invest. Dermatol.* 100:27–34).

3. Angiogenesis

Angiogenesis is the formation of new capillary blood vessels leading to neovascularization. Angiogenesis is a complex process which includes a series of sequential steps including endothelial cell-mediated degradation of vascular basement membrane and interstitial matrices, migration of endothelial cells, proliferation of endothelial cells, and formation of capillary loops by endothelial cells. Solid tumors are angiogenesis-dependent; i.e., as a small solid tumor reaches a critical diameter, for further growth it needs to elicit an angiogenic response in the surrounding normal tissue. The resultant neovascularization of the tumor is associated with more rapid growth, and local invasion. Further, an increase in angiogenesis is associated with an increased risk of metastasis. Therefore, antiangiogenic therapy to inhibit tumor angiogenesis would suppress or arrest tumor growth and its spread.

In normal physiological processes such as wound healing, angiogenesis is turned off once the process is completed. In contrast, tumor angiogenesis is not self-limiting. Further, in certain pathological (and nonmalignant) processes, angiogenesis is abnormally prolonged. Such angiogenesis-associated diseases include diabetic retinopathy, chronic inflammatory diseases including rheumatoid arthritis, dermatitis, and psoriasis. Antiangiogenic therapy would allow modulation in such angiogenesis-associated diseases having excessive vascularization.

4. Antiangiogenic Therapy and Vascular Targeting Therapy of Human Solid Tumors

The progressive growth of solid tumors beyond clinically occult sizes (e.g., a few $mm^3$) requires the continuous formation of new blood vessels, a process known as tumor angiogenesis. Tumor growth and metastasis are angiogenesis-dependent. A tumor must continuously stimulate the growth of new capillary blood vessels to deliver nutrients and oxygen for the tumor itself to grow. Therefore, either prevention of tumor angiogenesis (antiangiogenic therapy) or selective destruction of tumor's existing blood vessels (vascular targeting therapy) present a strategy directed to preventing or treating solid tumors.

Since a local network of new capillary blood vessels provide routes through which the primary tumor may metastasize to other parts of the body, antiangiogenic therapy should be important in preventing establishment of small solid tumors or in preventing metastasis (See, e.g., Folkman, 1995, *Nature Medicine*, 1:27–31). On the other hand, the vascular targeting therapy which attacks the existing vasculature is likely to be most effective on large tumors where the vasculature is already compromised (See, e.g., Bicknell and Harris, 1992, *Semin. Cancer Biol.* 3:399–407). Monoclonal antibodies, and fragments thereof according to the present invention are used as a means of delivering to either existing tumor vasculature or newly forming tumor neovascularization therapeutic compounds in a method of antiangiogenic therapy and vascular targeting therapy (collectively referred to as "antiangiogenic therapy").

5. Mouse Models for Human Disease

A. Athymic Nude or SCID Mouse Model

In the following embodiments used to illustrate the invention, it is important to consider the following concept. The use of athymic nude mice with human tumor xenografts has been validated as a model for the evaluation of chemotherapeutic agents because the model has been shown to reflect the clinical effectiveness of chemotherapeutic agents in original patients treated with these agents; and reflects antitumor effects from the agents, such as tumor regression or inhibition of tumor growth, as consistent with the activity against the corresponding types of clinical cancer (See for example, Neuwalt et al., 1985, *Cancer Res.* 45:2827–2833; Ovejera et al., 1978, *Annals of Clin. and Lab. Science* 8:50). SCID mice with human tumor xenografts has also been accepted by those skilled in the art as a model for the evaluation of chemotherapeutic agents.

Monoclonal antibodies are useful for selectively targeting tumors and for selective delivery of anticancer agents to tumor target tissue(s). In that regard, anti-endoglin mAbs may be used to target human tumor vasculature. Athymic nude mice or SCID mice with human tumor xenografts is a model in which may be tested antibody-directed targeting of tumor vasculature in a process of antiangiogenic therapy. The problem, however, is that the neovascularization for human xenografts in the mouse model arises from the (mouse) host's tissues. Thus, the prior art anti-endoglin mAbs, which are restricted to reactivity with either human endoglin or murine endoglin, cannot be used in such mouse models to perform the studies necessary to evaluate the clinical efficacy, pharmacokinetics, and the possibility of adverse side effects of antiangiogenic therapy. Therefore, there is a need for an anti-endoglin mAb which specifically binds to a cross-reactive epitope shared between endoglin on human and murine endothelial cells, wherein such mAbs are essential for performing animal model studies of human solid tumors.

B. Mouse Models for Angiogenesis-associated Diseases

In the following embodiments used to illustrate the invention, it is important to consider the following concept. The use of mouse models of angiogenesis has been accepted and validated as a models for the evaluation of therapeutic agents because the models have been shown to reflect the clinical parameters characteristic of the respective disease, as well as predictive of the effectiveness of therapeutic agents in patients. These mouse models include, but are not limited to: mouse model for retinal neovascularization (Pierce et al., 1995, *Proc. Natl. Acad. Sci. USA* 92:905–909); mouse models for rheumatoid arthritis (MRL-lpr/lpr mouse model, Folliard et al., 1992, *Agents Actions* 36:127–135; mev mouse, Kovarik et al., 1994, *J. Autoimmun.* 7:575–88); mouse models for angiogenesis (Majewski et al., 1994, *Int. J. Cancer* 57:81–85; Andrade et al., 1992, *Int. J. Exp. Pathol.*, 73:503–13; Sunderkotter et al., 1991, *Am. J. Pathol.* 138:931–939); mouse model for dermatitis (Maguire et al., 1982, *J. Invest. Dermatol.* 79:147–152); and mouse model for psoriasis (Blandon et al., 1985, *Arch. Dermatol. Res.* 277:121–125; Nagano et al., 1990, *Arch. Dermatol. Res.* 282:459–462). Thus, the prior art anti-endoglin mAbs, which are restricted to reactivity with either human endoglin or murine endoglin, cannot be used in the mouse model for the respective angiogenesis-associated disease to perform the studies necessary to evaluate the clinical efficacy, pharmacokinetics, and adverse side effects of antiangiogenic therapy in humans. Therefore, there is a need for an anti-endoglin mAb which specifically binds to a cross-reactive epitope shared between endoglin on human and murine endothelial cells, wherein such mAbs are essential for performing animal model studies of angiogenesis-associated diseases.

Hence, a need still exists for anti-endoglin mAbs which can be used in antiangiogenic therapy of human tumor angiogenesis, and of other human angiogenesis-associated diseases having excessive vascularization, which can be evaluated for clinical efficacy and pharmacokinetics in human xenograft-mouse models, or mouse models of angiogenesis-associated diseases.

SUMMARY OF THE INVENTION

Accordingly, it is a primary object of the present invention to provide anti-endoglin mAbs which can be used in anti-angiogenic therapy of human tumor angiogenesis.

It is another object of the present invention to provide anti-endoglin mAbs which can be used in antiangiogenic therapy of human angiogenesis-associated diseases having excessive vascularization.

It is another object of the present invention to provide such anti-endoglin mAbs, which can be used in antiangiogenic therapy, and which can be evaluated in the athymic nude or SCID mouse model or mouse models of angiogenesis-associated diseases.

It is another object of the present invention to provide a method for antiangiogenic therapy of human tumor angiogenesis using anti-endoglin mAbs.

It is a further object of the present invention to provide a method for antiangiogenic therapy of human angiogenesis-associated diseases having excessive vascularization using anti-endoglin mAbs.

The foregoing objects are achieved by providing novel anti-endoglin mAbs reactive against human endoglin which are also, unexpectedly, crossreactive with murine endoglin. The mAbs of the present invention may be conjugated to antitumor agents in providing a method for antiangiogenic therapy of human tumor vasculature. The mAbs of the present invention may be conjugated to angiogenesis inhibitors in providing a method for anti-angiogenic therapy of human angiogenesis-associated diseases having excessive vascularization. The mAbs of the present invention may also be used without being conjugated to any agents. These and further features and advantages of the invention will be better understood from the description of the preferred embodiments when considered in relation to the figures.

DETAILED DESCRIPTION OF THE PREFERRED EMBODIMENTS

Definitions

Figure 1A:
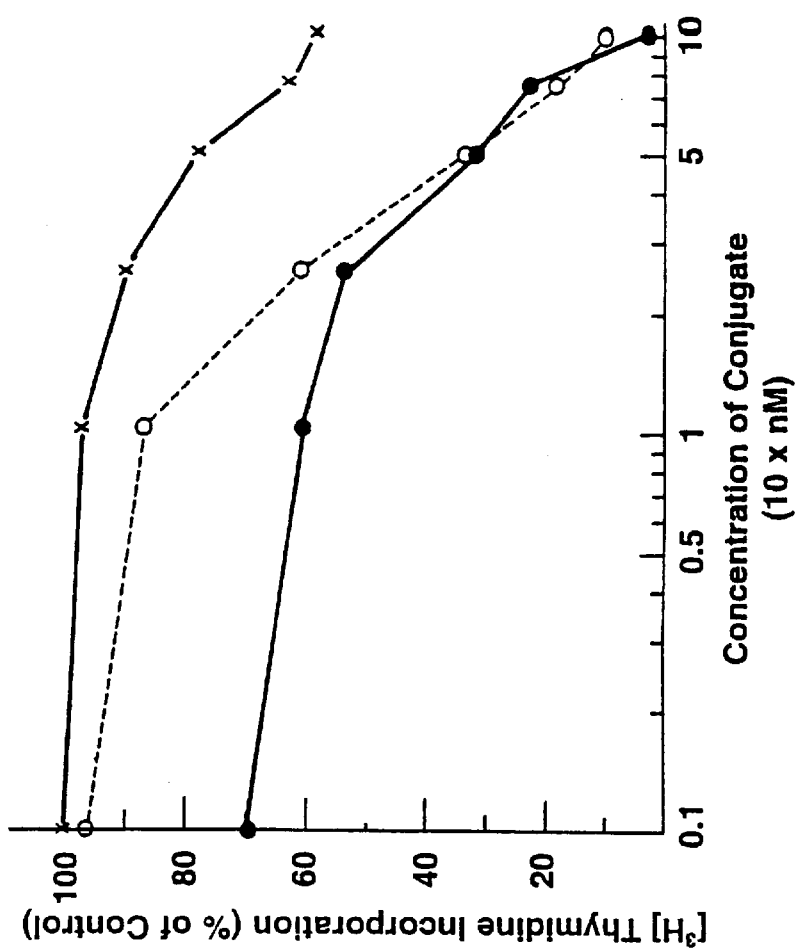
FIG. 1A is a graph depicting the cytotoxic activity against proliferating murine endothelial cells (SVEC4-10) of immuno-conjugates comprising the anti-endoglin mAbs of the present invention and ricin A chain (RA).

The term "angiogenesis-associated disease" is used herein, for purposes of the specification and claims, to mean certain pathological processes in humans where angiogenesis is abnormally prolonged. Such angiogenesis-associated diseases include diabetic retinopathy, chronic inflammatory diseases, rheumatoid arthritis, dermatitis, psoriasis, stomach ulcers, and most types of human solid tumors.

The term "angiogenesis inhibitor" is used herein, for purposes of the specification and claims, to mean a biomolecule including, but not limited to, peptides, proteins, enzymes, polysaccharides, oligonucleotides, DNA, RNA, recombinant vectors, and drugs which function to inhibit angiogenesis. Angiogenesis inhibitors are known in the art and include natural and synthetic biomolecules such as paclitaxel, O-(chloroacetyl-carbomyl) fumagillol ("TNP-470" or "AGM 1470"), thrombospondin-1, thrombospondin-2, angiostatin, human chondrocyte-derived inhibitor of angiogenesis ("hCHIAMP"), cartilage-derived angiogenic inhibitor, platelet factor-4, gro-beta, human interferon-inducible protein 10 ("IP10"), interleukin 12, Ro 318220, tricyclodecan-9-yl xanthate ("D609"), irsogladine, 8,9-dihydroxy-7-methyl-benzo[b] quinolizinium bromide ("GPA 1734"), medroxyprogesterone, a combination of heparin and cortisone, glucosidase inhibitors, genistein, thalidomide, diamino-antraquinone, herbimycin, ursolic acid, and oleanolic acid.

The term "antiangiogenic therapy" is used herein, for purposes of the specification and claims, to mean therapy targeted to vasculature expressing endoglin (expressed at higher levels on proliferating vasculature as compared to quiescent vasculature); whether the therapy is directed against angiogenesis (i.e., the formation of new capillary blood vessels leading to neovascularization), and/or existing vasculature and relating to a disease condition (e.g., vascular targeting therapy).

The term "antibody fragment" or "fragment thereof" is used herein, for purposes of the specification and claims, to mean a portion or fragment of an intact antibody molecule, wherein the fragment retains antigen-binding function; i.e., $F(ab')_2$, Fab', Fab, Fv, single chain Fv ("scFv"), Fd' and Fd fragments. Methods for producing the various fragments from mAbs are well known to those skilled in the art (see, e.g., Plückthum, 1992, *Immunol. Rev.* 130:152–188).

The terms "binding specificity for crossreactive epitopes shared by endoglin expressed on human vascular endothelial cells and endoglin expressed on murine vascular endothelial cells" (or alternatively, "binding specificity for crossreactive epitopes between human endoglin and murine endoglin") are used herein, for purposes of the specification and claims, to mean the property of an anti-endoglin antibody to bind a cross-reactive epitope present on both human endoglin and murine endoglin:

(a) wherein such epitope is accessible on the surface of the vascular endothelial cells expressing the endoglin;

(b) wherein the binding to the endoglin epitope present on murine endothelial cells is greater than the binding exhibited by an isotype control immunoglobulin, and wherein "greater than" can be measured quantitatively as the binding of the anti-endoglin mAb minus one standard deviation needs to be larger than the binding of the isotype control immunoglobulin plus 1 standard deviation, as will be more apparent in the following examples; and (c) wherein the binding of the anti-endoglin antibody to the endoglin expressed on murine endothelial cells is at least two fold less when compared to the binding of the anti-endoglin antibody to the endoglin expressed on human endothelial cells, as detected in a standard assay for immunoreactivity.

The term "immunoconjugate" is used herein, for purposes of the specification and claims, to mean a conjugate comprised of the anti-endoglin mAbs or a fragment thereof according to the present invention (or alternatively, an anti-endoglin mAb, or fragment thereof, that recognizes human vascular endothelial cells but lacks crossreactivity with mouse endoglin) and at least one antitumor agent or at least one angiogenesis-inhibitor. Such antitumor agents are known in the art and include, but not limited to, toxins, drugs, enzymes, cytokines, radionuclides, photodynamic agents, and angiogenesis inhibitors. Toxins include ricin A chain, mutant Pseudomonas exotoxins, diphtheria toxoid, streptonigrin, boamycin, saporin, gelonin, and pokeweed antiviral protein. Drugs include daunorubicin, methotrexate, and cali-cheamicins. Radionuclides include radiometals. Cytokines include transforming growth factor (TGF)-β, interleukins, interferons, and tumor necrosis factors. Photodynamic agents include porphyrins and their derivatives.

The methods for complexing the anti-endoglin mAbs or a fragment thereof with at least one antitumor agent are well known to those skilled in the art (i.e., antibody conjugates as reviewed by Ghetie et al., 1994, *Pharmacol. Ther.* 63:209–34). Often such methods utilize one of several available heterobifunctional reagents used for coupling or linking molecules.

The term "isotype control immunoglobulin" is used herein, for purposes of the specification and claims, to mean a species specific (e.g. raised in the same species as the antibody to which it is compared), isotype-matched (e.g., of the same immunoglobulin (Ig) class and subclass as the antibody to which it is compared) Ig which does not bind with specificity to the antigen to which the compared antibody has binding specificity, as will be more apparent from the following embodiments.

The term "mammalian host" or "host" is used herein, for purposes of the specification and claims, to mean a mouse or a human.

The term "monoclonal antibody", as denoted as having binding specificity for a crossreactive epitope, is used herein, for purposes of the specification and claims, to mean murine monoclonal antibodies and engineered (e.g., recombinant) antibody molecules made therefrom in which the binding specificity for a crossreactive epitope shared between human endoglin and murine endoglin is maintained; and includes chimeric or "humanized" antibodies, as will be more apparent from the following embodiments.

The term "tumor" is used herein, for purposes of the specification and claims, to mean a tumor expressing endoglin at moderate to high levels (as compared to expression by normal tissue of the same type) such as human leukemias, including non-T-cell-type (non-T) acute lymphoblastic leukemia (ALL), myelo-monocytic leukemia; and human solid tumors, with its surrounding vasculature expressing endoglin at moderate to high levels (as compared to expression by normal tissue of the same type) including angiosarcoma, breast carcinoma, cecum carcinoma, colon carcinoma, Hodgkins lymphoma, lymphoma, lung carcinoma, melanoma, osteosarcoma, ovarian carcinoma, parotid tumor, pharyngeal carcinoma, prostate carcinoma, and rectosigmoid carcinoma.

A drawback to conventional chemotherapy and radiotherapy is the lack of selectively delivering the therapy to its intended target, diseased tissue, rather than to normal tissue. Monoclonal antibodies have been used to deliver therapeutics with greater target specificity, thereby reducing toxicity. Murine mAbs or fragments thereof have been used to treat human disease, often with modest to substantial clinical efficacy (see, e.g., Ghetie et al., 1994, supra). Studies show that murine monoclonal antibodies may be repeatedly given on a safe basis, even if a human anti-mouse antibody response develops. Additionally, a human anti-mouse antibody response did not cause significant clinical problems with further repeated infusions of the murine mAb in some cases (see, e.g., Frodin et al., 1992, *Cell Biophys.* 21:153–165).

Antiangiogenic therapy may overcome some of the major problems associated with conventional chemotherapy or immunotherapy of human solid tumors. First, antiangiogenic therapy may allow circumvention of the problem of acquired drug resistance. Drug-resistant tumor mutants are easily generated because of the genetic instability of tumor cells. However, genetically-stable normal cells, such as vascular endothelial cells, would be far less adept at generating drug resistance. In that regard, drug resistance has not been a significant problem in studies involving the use of antiangiogenic agents (Folkman, 1995, *Nature Medicine* 1:27–31). Additionally, antiangiogenic therapy may overcome the problem of tumor heterogeneity for the reasons as applied above. Further, physiologic barriers for high molecular weight drugs (such as mAbs and immunoconjugates) to penetrate into solid tumors will be circumvented by targeting a tumor's vasculature rather than tumor cells. This is because the therapeutic agent delivered in antiangiogenic therapy selectively acts on the vascular endothelial cells lining the blood vessels of the tumor rather than the tumor cells themselves (although it is appreciated by those skilled in the art that the delivered therapeutic agent may secondarily act on tumor cells with which it comes in contact). Vascular endothelial cells are directly accessible to circulating high molecular weight drugs/antitumor agents. Furthermore, destruction of all tumor-associated blood vessels is not necessary for effective antiangiogenic therapy. This is because large numbers of tumor cells are critically dependent upon a small number of capillary endothelial cells. If a capillary bed is damaged as a result of antiangiogenic therapy, a significant number of tumor cells will die of nutrient and oxygen deprivation. An additional advantage is that a single type of therapeutic agent developed for antiangiogenic therapy may be applied to many types of solid tumors and angiogenesis-associated diseases.

One embodiment of the present invention comprises a novel class of murine mAbs characterized by their binding specificity for crossreactive epitopes between human endoglin and murine endoglin; stronger immunoreactivity with human endoglin as compared to murine endoglin; and selective immunoreactivity which is restricted to certain tumor vasculature and proliferating vascular endothelial cells, as characteristic of angiogenesis. Thus, unlike the prior art anti-endoglin mAbs which are restricted to reactivity with either human endoglin or murine endoglin, the anti-endoglin mAbs of the present invention can be used in the athymic nude mouse model, SCID (severe combined immunodeficiency) mouse model, or other mouse models of angiogenesis-associated diseases to perform the studies necessary to evaluate clinical efficacy, pharmacokinetics, and potential adverse side effects of antiangiogenic therapy in humans. Four such anti-endoglin mAbs have been developed to date: mAbs Y4-2F1, K4-2C10, P3-2G8, and D4-2G10. Hybridomas expressing either of the mAbs Y4-2F1, K4-2C10, P3-2G8, and D4-2G10 have been deposited with the American Type Culture Collection (ATCC, Rockville, Md.) under Designation Nos. HB-12171, HB-12172, HB-12173, and HB-12174, respectively. A specific embodiment illustrating this novel class of the anti-endoglin mAbs according to the present invention is mAb K4-2C10.

Another embodiment of the present invention comprises a method for using anti-endoglin mAbs, or a fragment thereof, according to the present invention in antiangiogenic therapy. In this embodiment, an immunoconjugate is formed by coupling an anti-endoglin mAb, or a fragment thereof, to at least one anti-tumor agent, wherein the resultant immunoconjugate retains its selective immunoreactivity restricted to certain tumor vasculature and proliferating vascular endothelial cells characteristic of angiogenesis. In another embodiment, the anti-endoglin antibody may be administered without being conjugated to any agent. The immunoconjugate or the unconjugated antibody is administered to an appropriate mouse model for testing the antiangiogenic therapy, with administration dependent upon the location of target vasculature. Having evaluated parameters such as clinical efficacy and pharmacokinetics in the appropriate mouse model, the antiangiogenic therapy may then be "scaled up" to human treatment. A physiological basis for scaling up the therapeutic agents comprising mAbs from a mouse model to humans is known to those skilled in the art (see, e.g., Baxter et al., 1995, *Cancer Res.* 55:4611–4622, herein incorporated by reference).

Demonstrated herein is the efficacy of anti-endoglin mAbs, having binding specificity for a crossreactive epitope between human endoglin and murine endoglin, to inhibit tumor-associated angiogenesis, and inhibit vasodilation of preexisting small blood vessels (vascular-targeting). Since it is believed the present results demonstrate for the first time that an anti-endoglin mAb, or an immunoconjugate containing the same, can effectively target tumor-associated vasculature in vivo, another embodiment of the present invention is a method of antiangiogenic therapy which utilizes any anti-endoglin mAb recognizing endoglin expressed on human vasculature endothelial cells, regardless of whether the mAb is cross-reactive or not crossreactive with endoglin expressed on murine endothelial cells. More particularly, because the anti-endoglin mAbs of the present invention exhibit both immunoreactivity to both mouse and human endoglin and therapeutic efficacy in targeting tumor-associated vasculature in vivo, such mAbs establish reasonably predictive utility in humans for themselves and for mAbs that recognize only endoglin on the surface of human vascular endothelial cells. It is believed that previous to the illustrations herein, there are no published reports of anti-endoglin mAbs or immunoconjugates containing anti-endoglin mAbs having efficacy in antiangiogenic therapy.

EXAMPLE 1

Production of Crossreactive Anti-endoglin mAbs

At the time of the present invention, the previously reported anti-endoglin mAbs were generated by immunizing mice with crude preparations containing endoglin, including glyco-protein mixtures from cell membranes, whole cell suspensions of leukemia cells, inflamed skin, and human umbilical vein endothelial cells. The specificity of the anti-endoglin mAbs so produced were reported to be either to human endoglin or to mouse endoglin. In contrast, the crossreactive anti-endoglin mAbs of the present invention were generated by immunization of mice with purified human endoglin ("hEDG"). Although not intending to be bound to any theory of action, it is believed that the use of purified endoglin as an antigen to generate anti-endoglin mAbs facilitated generation of mAbs having binding specificity for crossreactive epitopes between human endoglin and murine endoglin. In that regard, previous to the invention disclosed herein there are believed to be no published reports describing anti-endoglin mAbs that crossreact with human and mouse endoglins; and that a substantial proportion (i.e., 4 of 11 of the anti-endoglin mAbs generated using purified human endoglin (hEDG)) demonstrated the cross-reactivity between human and mouse endoglins. Further, it is known in the art that for generating a mAb, a partially purified soluble antigen may contain immuno-dominant components which contibute disproportionately to the antibody response (Milstein and Lennox, 1980, In: *Current Topics in Developmental Biology* 14:1–32).

hEDG was purified from human acute lymphoblastic leukemia (ALL) cells. Cell membrane glycoproteins were isolated using detergent extraction and lectin affinity chromatography as described previously (Haruta and Seon, 1986, *Proc. Natl. Acad. Sci. USA,* 83:7898–7902, herein incorporated by reference). The isolated glycoproteins were applied to an immunoaffinity column containing anti-endoglin mAb SN6 (Haruta and Seon, 1986, supra) which had been equilibrated with 25 mM Tris-HCl, pH 8.0 containing 0.5% taurocholate, 0.15 M NaCl, 2 mM EDTA, 0.03% NaN$_3$ and 0.5 mM phenylmethylsulfonyl fluoride. The bound materials were eluted with 50 mM diethylamine-HCl, pH 11.3 containing 0.5% taurocholate, 2 mM EDTA, 0.03% NaN$_3$ ("alkaline buffer"). The eluate was immediately neutralized by the addition of one-tenth volume of 0.5 M Tris-HCl buffer, pH 7.1. The eluted material was reapplied to the immunoaffinity column and the bound material was eluted with the alkaline buffer further containing 0.0% cytochrome-c (a 12.4 kD carrier protein) and neutralized. The eluted material was dialyzed and concentrated using ultrafiltration (e.g., with a YM-10 membrane). This purification process was carried out at 4–6° C. Purification of hEDG was monitored by a solid phase radioimmunoassay using mAb SN6, and confirmed by gel electrophoresis with silver staining. The resultant hEDG preparation contained a single major component of 170 kD under unreduced conditions, and 92 kD under reduced conditions.

In a first immunization protocol, 2 female BALB/c mice were immunized with the isolated hEDG following an immunization protocol described previously (Seon et al., 1983, *Proc. Natl. Acad. Sci. USA*, 80:845–849) with modifications. Briefly, an antigen solution comprising 10 µg of the hEDG preparation in 100 µl of 10 mM Tris-HCl buffer, pH 7.5, with 0.5% taurocholate, 0.15 M NaCl, and 14 µg cytochrome-c, was mixed with an equal volume of adjuvant (e.g., Fruend's complete) and then injected subcutaneously at multiple sites on each of the mice. In addition, 1×10$^9$ *Bordetella pertussis* bacteria in 100 µl saline were injected at different sites. Two booster immunizations of the antigen solution in adjuvant were administered subcutaneously. A last immunization comprising 40 µl antigen solution containing 8 µg hEDG preparation mixed with 200 µl saline was administered intraperitoneally. The spleens were removed and fused with P3/NS1/1-Ag4-1 (NS-1) mouse myeloma cell line 4 days after the last immunization. Cell fusion, hybridoma screening, and immunoglobulin class determination were performed as described previously (Haruta and Seon, 1986, supra). In a second immunization protocol, a female BALB/c mouse was immunized with the isolated hEDG as described for the first experiment, but without the administration of *B. pertussis*. Eleven hybridomas generated by these immunizations produce individually different anti-hEDG mAbs that were further characterized. As described in the following embodiment, four of the eleven mAbs generated using these immunization protocols demonstrated binding specificity for crossreactive epitopes between human endoglin and murine endoglin.

EXAMPLE 2
Characterization of Anti-endoglin mAbs

In this embodiment is illustrated the binding specificity of four of the eleven different anti-human endoglin antibodies generated using the methods according to Example 1. These four mAbs, K4-2C10, D4-2G10, Y4-2F1 and P3-2G8, which react with endoglin expressed on human cells were found to crossreact with endoglin expressed on murine cells. This crossreactivity is an unexpected result since (a) it has not been reported previously; (b) there is significantly less identity in the murine and human sequences encoding the extracellular region (exposed to antibody) of endoglin than that encoding the transmembrane regions and cytoplasmic regions; and (c) generation of such an antibody in mice is an autoimmune phenomenon, a result that one skilled in the art would not reasonably expect. Regarding the latter, the result is unexpected since the cross-reactive antibodies recognize "self" or a murine component; and an individual does not normally make an immune response to self components (see, e.g., Austin and Wood, in *Principles of Cellular and Molecular Immunology*, Oxford University Press, 1993).

mAbs K4-2C10, Y4-2F1 and P3-2G8 were generated using the immunization protocol first described in Example 1, whereas D4-2G10 was generated using the second immunization protocol. The specificity of immunoreactivity of each of these four mAbs was further characterized by testing them against various hematopoietic cell lines in a cellular radioimmunoassay (RIA) and by immunoprecipitation of hEDG using methods previously described (Haruta and Seon, 1986, supra). Briefly, 20 µl of a 1:9 dilution of the culture fluids of individual hybridomas and 2×10$^5$ hematopoietic cells in each test by RIA. Mouse plasmacytoma IgG1 and IgG2a were included in the assays as controls. The results indicating immunoreactivity (+) or no detectable immunoreactivity (−) are shown in Table 1.

TABLE 1

| Cell line | Origin | K4-2C10 | D4-2G10 | Y4-2F1 | P3-2G8 |
|---|---|---|---|---|---|
| KM-3 | ALL | + | + | + | + |
| NALM-16 | ALL | + | + | + | + |
| REH | ALL | + | + | ND | ND |
| NALM-6 | ALL | + | + | + | + |
| NALM-1 | CML-BC | + | + | ND | ND |
| BALL-1 | ALL | − | − | − | − |
| BALM-2 | ALL | − | − | ND | ND |
| Daudi | BL | − | − | − | − |
| Ramos | BL | − | − | ND | ND |
| U698M | LS | − | − | ND | ND |
| BALM-3 | LY | − | − | ND | ND |
| SU-DHL-4 | HL | − | − | ND | ND |
| MOLT-4 | ALL | − | − | − | − |
| JM | ALL | − | − | − | − |
| CCRF-CEM | ALL | − | − | ND | ND |
| CCRF-HSB2 | ALL | − | − | ND | ND |
| Ichikawa | ALL | − | − | ND | WD |
| HPB-MLT | LTL | − | − | ND | WD |
| HUT-78 | SS | − | − | ND | ND |
| HL-60 | APL | + | + | + | + |
| U937 | HL | + | + | + | + |
| ML-2 | AML | + | + | ND | ND |
| CCRF-SB | | − | − | − | − |
| RPMI 8057 | | − | − | ND | ND |
| RPMI 1788 | | − | − | ND | ND |

ALL- acute lymphoblastic leukemia; CML-BC- chronic myelocytic leukemia in blst crisis; BL- Burkitt's lymphoma; LS- lymphosarcoma; LY- lymphoma; HL- histiocytic lymphoma; LTL- leukemic phase of T-cell lymphoma; SS- Sezary syndrome; APL- acute promyelocytic leukemia; AML, acute myelocytic leukemia; ND- not determined.

As shown by Table 1 for the anti-endoglin mAbs of the present invention, and as previously determined for control anti-endoglin mAb SN6, immunoreactivity was demonstrated for the immature B-lineage leukemia cell lines tested (KM-3, REH, NALM-1, NALM-6 and NALM-16) and the myelo-monocytic leukemia cell lines tested (ML-2, HL-60 and U937). However, they did not react with any of the mature B-lineage leukemia-lymphoma cell lines (BALL-1, BALM-2, BALM-3, Daudi, Ramos, U698M, and SU-DHL-4), any of the T leukemia cell lines (MOLT-4, JM, CCRF-CEM, CCRF-HSB2, Ichikawa, HPB-MLT and HUT-78), nor the EBV-transformed B cell lines (CCRF-SB, RPMI 1788 and RPMI 8057). The immunoprecipitation assay showed that all four anti-endoglin mAbs of the present invention, as did the control anti-hEDG mAb SN6, precipitated a 170 kD component under unreduced conditions and a 92 kD component under reduced conditions.

Using RIA, the 11 anti-hEDG mAbs generated using the protocols according to Example 1 and anti-hEDG mAb SN6 were tested for immunoreactivity to proliferating SVEC4-10 murine endothelial cells expressing endoglin at their cell surface. As shown in Tables 2 and 3, only the four mAbs K4-2C10, D4-2G10, Y4-2F1 and P3-2G8 were found to react significantly with the endoglin expressed on the murine endothelial cells (greater than the binding exhibited by the isotype control Ig+1 std. deviation) in exhibiting binding specificity for crossreactive epitopes shared by endoglin expressed on human vascular endothelial cells and endoglin expressed on murine vascular endothelial cells.

TABLE 2

Immunoreactivity with murine endothelial cells as determined by RIA (cpm ± std. deviation)

| mAb | 2 hrs. |
|---|---|
| K4-2C10 | 549 ± 17 |
| D4-2G10 | 617 ± 24 |
| SN6 | 421 ± 85 |
| isotype control | 419 ± 30 |

Note SN6 binding of 421 ± 85 is not greater than the binding exhibited by the isotype control Ig because 421 minus 1 std. deviation (336) is not greater than the isotype control Ig plus one std. deviation (449).

TABLE 3

| Cells | mAb | 2 hr. | 4 hr. | 8 hr. | 24 hr. | 32 hr. |
|---|---|---|---|---|---|---|
| SVEC4-10 | K4-2C10 | 414 ± 46 | 458 ± 62 | 698 ± 44 | 926 ± 32 | 785 ± 102 |
|  | D4-2G10 | 445 ± 85 | 572 ± 75 | 1,018 ± 164 | 1,222 ± 62 | 863 ± 170 |
|  | Y4-2F1 | 381 ± 15 | ND | ND | 758 ± 64 | ND |
|  | P3-2G8 | 394 ± 36 | ND | ND | 662 ± 30 | ND |
|  | Control | 290 ± 29 | 267 ± 13 | 463 ± 58 | 456 ± 60 | 449 ± 104 |
| HUVEC | K4-2C10 | 8,227 ± 385 | ND | ND | 11,346 ± 1,026 | ND |
|  | D4-2G10 | 7,960 ± 388 | ND | ND | 13,077 ± 876 | ND |
|  | Control | 196 ± 24 | ND | ND | 224 ± 25 | ND |

Each test was carried out in triplicate and the values given (as counts per minute) are the mean of triplicates ± standard deviation.

The crossreactivity of these four mAbs to murine SVEC4-10 cells is compared with the immunoreactivity of mAbs K4-2C10 and D4-2G10 to human umbilical vein endothelial cells (HUVEC; high expressors of hEDG), at various incubation times in the RIA (2 hours, 4 hours, 8 hours, 24 hours, and 32 hours) as shown in Table 3. The isotype control antibodies are respective species-specific, isotype-matched IgG.

In addition, strong immunoreactivity of the four crossreactive anti-endoglin mAbs (e.g., K4-2C10, D4-2G10, Y4-2F1 and P3-2G8) with human endothelial cells (e.g., human umbilical vascular endothelial cells-HUVEC) was detected in flow cytometric analysis. In contrast, rat mAb clone MJ7/18 (commercially available from Pharmingen; see also Ge and Butcher, 1994, Gene 138:201–206) which reacts with mouse endoglin, failed to cross-react with endoglin expressed on human vascular endothelial cells (e.g., immunoreactivity was less than the immunoreactivity demonstrated by the isotype control Ig) in the cellular RIA, as shown in Table 4.

TABLE 4

Immunoreactivity with human endothelial cells as determined by RIA (cpm ± std. deviation)

| Antibody | 2 hours |
|---|---|
| mAb MJ7/18 | 185 ± 14 |
| rat isotype control Ig | 330 ± 18 |

The specificity of immunoreactivity of each of the four mAbs K4-2C10, D4-2G10, Y4-2F1 and P3-2G8 was further characterized by using these mAbs in histochemical staining of several human malignant tissues. The tissues included malignant tissues of breast, colon, kidney, lung, and lymph node. The tissues were frozen, then air-dried and fixed with acetone, and stained according to the methods standard in the art. The immunohistochemical staining of the malignant tissue with each of the four mAbs showed that these mAbs reacted strongly with the vascular endothelium associated with all of the malignant tissues tested, whereas the isotype control IgG failed to demonstrate any significant staining in each tissue.

In summary, the anti-hEDG mAbs according to the present invention showed strong immunoreactivity to endoglin as expressed by human vascular endothelial cells, as demonstrated by their reactivity with HUVEC and malignant tumor vasculature. It is important to note that the immunoreactivity was to the vasculature of the malignant tumor tissue, and not to the tumor cells per se. The anti-hEDG mAbs according to the present invention also reacted significantly with the endoglin expressed on proliferating murine endothelial cells, although to a lesser degree (quantitatively at least 2 fold less) as compared to the immunoreactivity with that on HUVEC. Since endoglin is primarily a proliferation-associated marker for endothelial cells undergoing active angiogenesis, the anti-hEDG mAbs according to the present invention may be used to selectively target antiangiogenic therapy to tumor vasculature or the excessive vascularization present in other angiogenesis-associated diseases in both humans, and mouse models of human disease(s).

Any potentially new agents for antiangiogenic therapy need to be evaluated for their safety and efficacy in an animal model before the agents are applied to the clinical trials involving human patients. In this regard, the observed cross-reactivity of the anti-human endoglin mAbs according to the present invention with mouse endothelial cells is critically important for evaluating safety and efficacy of these mAbs and immunoconjugates formed using these mAbs. Having established therapeutic efficacy in targeting tumor-associated vasculature in vivo, another embodiment of the present invention is the use of mAbs that recognize only endoglin on the surface of human vascular endothelial cells (e.g., and not murine endoglin) in targeting tumor-associated vasculature in vivo in humans.

EXAMPLE 3

In this example are illustrated various embodiments of a method according to the present invention for targeting therapies against tumor vasculature or the excessive vascularization present in other angiogenesis-associated diseases (collectively referred to as "antiangiogenic therapy"). The method of antiangiogenic therapy according to the present invention is a primary utility for the anti-endoglin mAbs according to the present invention, and for anti-endoglin mAbs that recognize only human vascular endothelial cells (e.g., not crossreactive with mouse endoglin). Illustrated in the first and second embodiments is an immuno-conjugate produced using an anti-endoglin mAb according to the present invention, or a fragment thereof. The anti-endoglin mAb or a fragment thereof is coupled to either at least one antitumor agent, such as an angiogenesis inhibitor, in forming the immuno-conjugate. Illustrated in the third embodiment, is the use of unconjugated anti-endoglin mAb, or a fragment thereof, for antiangiogenic therapy. The above immunoconjugate or the unconjugated antibody is then used in a relevant mouse model to test the antiangiogenic therapy before scale up to antiangiogenic therapy in humans.

While the immunoconjugate or the unconjugated antibody may be administered by routes other than intravenously (i.v.), a preferred embodiment of the illustration is i.v. administration. This is because it is primarily the proliferating vasculature comprising the angiogenesis that is the target of the therapy; and thus, administering the immunoconjugate or the unconjugated antibody or a fragment thereof, intravenously saturates the targeted vasculature much quicker than if another route of administration is used. Additionally, the intravenous route allows for the possibility of further targeting to specific tissues. Thus, in a variation of this embodiment, a catheter may be used to direct the immunoconjugate or the unconjugated antibody or a fragment thereof, to the location of the target angiogenesis. For example, if tumor angiogenesis is the target of the antiangiogenic therapy, and if the tumor is located in the liver, then the immunoconjugate or the unconjugated antibody or a fragment thereof may be delivered into the hepatic portal vein using a catheter. In this variation, there is even less systemic distribution of the immunoconjugate or the unconjugated antibody or a fragment thereof, thereby further minimizing any potential side effects from antiangiogenic therapy. Using similar methods of production and administration described herein, immunoconjugates or the unconjugated antibody or a fragment thereof can be formed using anti-endoglin mAbs that recognize only human vascular endothelial cells.

1. Production of the Immunoconjugates

To illustrate the first embodiment, an immunoconjugate was prepared using each of the four anti-endoglin mAbs according to the present invention. The immunoconjugate comprises one of mAbs K4-2C10, D4-2G10, Y4-2F1 and P3-2G8 coupled to either ricin A chain ("RA") or deglycosylated ricin A chain ("dgRA") using a hetero-bifunctional reagent (SMPT) which introduces an in vivo-stable disulfide linker into the IgG molecules of the mAb (see, e.g., Thorpe et al., 1987, *Cancer Res.* 47:5924–5931). The RA or dgRA is then mixed and incubated with the modified mAb. The resultant mAb-dgRA conjugates or mAb-RA conjugates are separated from the unbound dgRA or RA, respectively, and then further purified. A control immunoconjugate is formed in the same manner but with the IgG component being an isotype-matched control IgG (e.g., MOPC 195 variant).

2. In Vitro Cytotoxic Activity of the Immunoconjugates

Figure 1B:
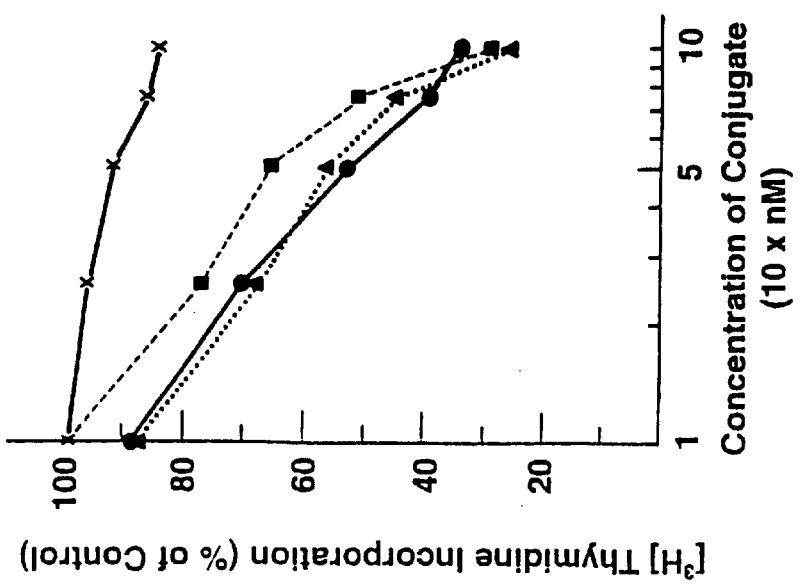
FIG. 1B is a graph depicting the cytotoxic activity against proliferating murine endothelial cells (SVEC4-10) of immuno-conjugates comprising the anti-endoglin mAbs of the present invention and deglycosylated ricin A chain (dgRA).

The in vitro cytotoxic activity of the various mAb-dgRA conjugates, mAb-RA conjugates, and control conjugate was evaluated by a modified method of May et al. (1990, *J. Immunol.* 144: 3637–3642). Briefly, proliferating SVEC4-10 murine endothelial cells, or MCF-7 human breast cancer cells, were distributed into wells of flat-bottomed 96-well microtiter plates at $2.5 \times 10^4$ cells/well. Varying amounts of the mAb-dgRA conjugates, mAb-RA conjugates, control conjugate, or culture medium (additional control) were added to the wells. The plates were then incubated for 48 hours at 37° C. in 5% $CO_2$. The cells contained in the wells were then pulsed with 1 $\mu$Ci/well [$^3$H] thymidine for 18 hours, and harvested on glass fiber filters using a semiautomatic cell harvester. The radioactivity was determined using a scintillation counter, and the results were expressed as a percentage of the [$^3$H]thymidine incorporated by cells treated with medium only. As shown in FIG. 1A, mAb-RA conjugates (K4-2C10-RA:●; Y4-2F1-RA:▲; & P3-2G8-RA:■) showed significantly more cytotoxicity against the proliferating murine endothelial cells compared to the cytotoxicity by the control-RA conjugate (x). Likewise, and as shown in FIG. 1B, mAb-dgRA conjugates (K4-2C10-dgRA:●; D4-2G10-dgRA:○) showed significantly more cytotoxicity against the proliferating murine endothelial cells compared to the cytotoxicity by the control-dgRA conjugate. The control conjugates showed weak and non-specific cytotoxic effects when concentrations were higher than 25 nM. Such nonspecific cytotoxic effects at these concentrations have been observed before (see, e.g., Seon, 1984, *Cancer Res.* 44:259–264). There was no significant cytotoxicity observed for the mAb-dgRA conjugates, and control conjugates against the MCF-7 human breast cancer cells.

3. Antiangiogenic Therapy Using the Immunoconjugates

A mAb-dgRA conjugate, K4-2C10-dgRA, was used to illustrate the antiangiogenic therapy according to the method of the present invention. A mAb-dgRA conjugate was selected for illustrative purposes since conjugates containing dgRA appear more efficacious than conjugates containing RA in in vivo tumor therapy when administered i.v. (see, e.g. Fulton et al., 1988, *Cancer Res.* 48:2626–2631).

A. Before the immunoconjugate is administered to a mouse model for human disease, a determination should be made of the maximum tolerated dose. In that regard, the $LD_{50}$ value of the K4-2C10-dgRA conjugate was determined using a modification of the method described by Fulton et al. (1988, supra). Briefly, groups of 4 female BALB/c mice (7 weeks old) were given intraperitoneal or intravenous injections of the K4-2C10-dgRA conjugate at doses of 0.025, 0.05, 0.1, 0.2, and 0.4 mg. The mice were weighed prior to injection, and daily thereafter, and were observed for morbidity and mortality for 2 weeks. The $LD_{50}$ value was determined by plotting the percentage of mortality versus injected dose to determine the dose resulting in 50% mortality. The $LD_{50}$ value of the K4-2C10-dgRA conjugate in mice was 16.4 $\mu$g/g body weight, and 14.8 $\mu$g/g body weight by intraperitoneal injections and intravenous injections, respectively.

B. SCID mice with human tumor xenografts comprising MCF-7 human breast cancer cells was a model for the evaluation of antiangiogenic therapy comprising administration of K4-2C10-dgRA conjugate. Human breast cancer was used in this model to represent human solid tumors. To produce this model, MCF-7 cells were transplanted into SCID mice. Preliminary dose-dependent titration experiments showed that all SCID mice inoculated subcutaneously with a dose of $8 \times 10^6$ cells/mouse developed subcutaneous tumors. Thus, $8 \times 10^6$ cells was the dosage used to establish subcutaneous tumors in the mice to be treated with the antiangiogenic therapy according to the present invention. Growth of the tumors was monitored daily.

C. In a first embodiment and second embodiment, the antiangiogenic therapy comprising administration of K4-2C10-dgRA conjugate was tested in the SCID mouse-MCF-7 xenograft model. Two sets of therapeutic protocols were carried out. In a first therapeutic protocol, a first group of 8 SCID mice that were inoculated subcutaneously with $8 \times 10^6$ MCF-7 cells/mouse were untreated (control). A second group of 8 SCID mice that were inoculated subcutaneously with $8 \times 10^6$ MCF-7 cells/mouse were treated by i.v. administration of 17 µg/0.2 ml unconjugated (free) mAb K4-2C10. A third group of 8 SCID mice that were inoculated subcutaneously with $8 \times 10^6$ MCF-7 cells/mouse were treated by i.v. administration with 20 µg/0.2 ml K4-2C10-dgRA conjugate. A fourth group of 8 SCID mice that were inoculated subcutaneously with $8 \times 10^6$ MCF-7 cells/mouse were treated by i.v. administration of unconjugated (free) mAb K4-2C10 (75 µg) followed by i.v. administration with the K4-2C10-dgRA conjugate (20 µg/0.2 ml) on days 3, 5, and 7 post tumor inoculation. Unconjugated mAb K4-2C10, for pretreating the mice comprising group 4, was administered 2 hours post tumor inoculation. The sterilized solutions of the unconjugated mAb K4-2C10, and of the K4-2C10-dgRA conjugate, were diluted with sterile PBS containing mouse serum albumin (0.05% final concentration) before injection via the tail vein of the mice. The total dose of this therapeutic protocol, $3 \times 20$ µg, of the immunoconjugate corresponded to 24% of the $LD_{50}$ dose.

During the treatment, the mice were monitored daily for tumor size and for morbidity, and weight of the mice was measured twice each week. Tumor volumes were estimated according to the following equation:

$$V = length + (width)^2 \times n/6$$

Figure 2A:
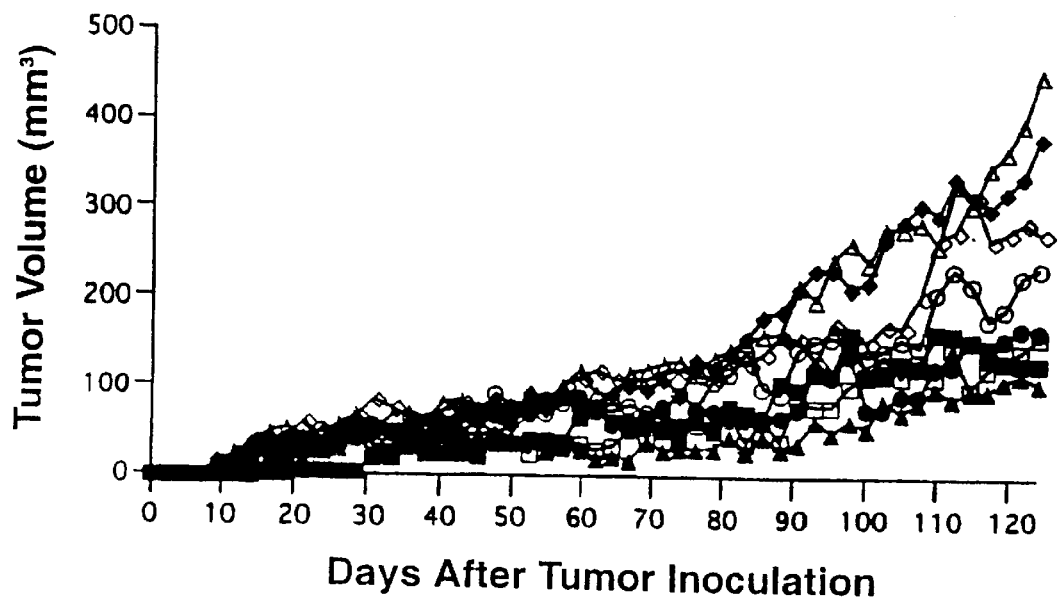
FIG. 2A is a graph depicting the progression in SCID mice of a human xenograft consisting of breast cancer cells (MCF-7).
Figure 2B:
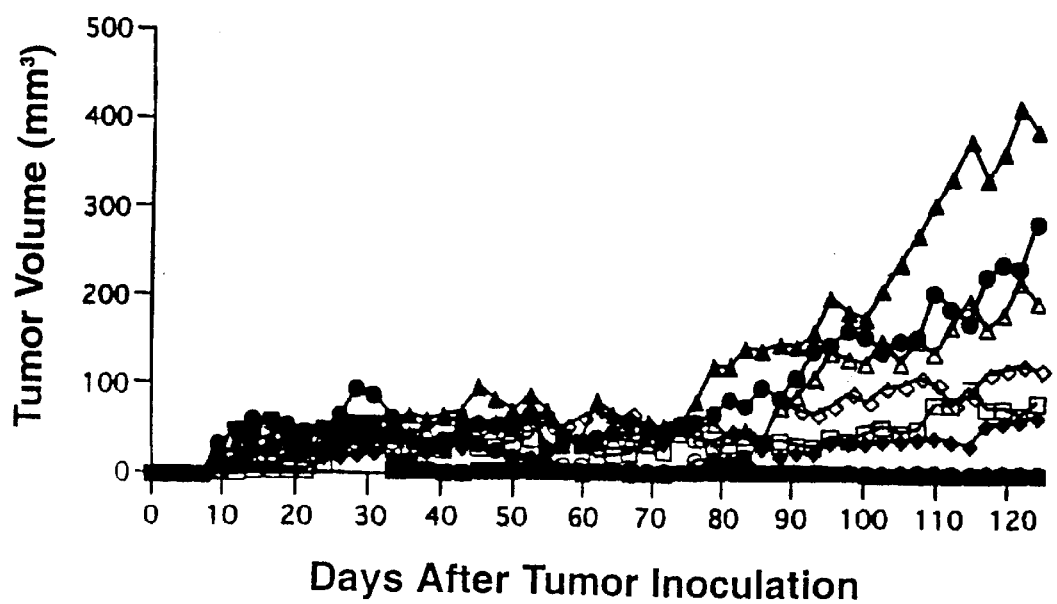
FIG. 2B is a graph depicting the progression in SCID mice of a human xenograft consisting of breast cancer cells (MCF-7), following treatment with unconjugated mAb K4-2C10.
Figure 2C:
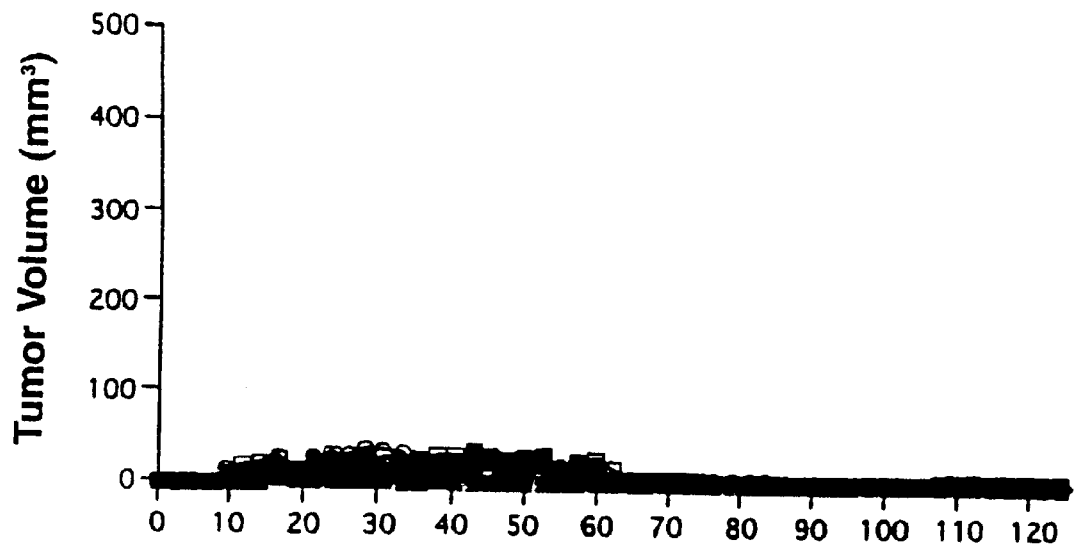
FIG. 2C is a graph depicting the progression in SCID mice of a human xenograft consisting of breast cancer cells (MCF-7), following treatment with an immunoconjugate (K4-2C10-dgRA conjugate).
Figure 2D:
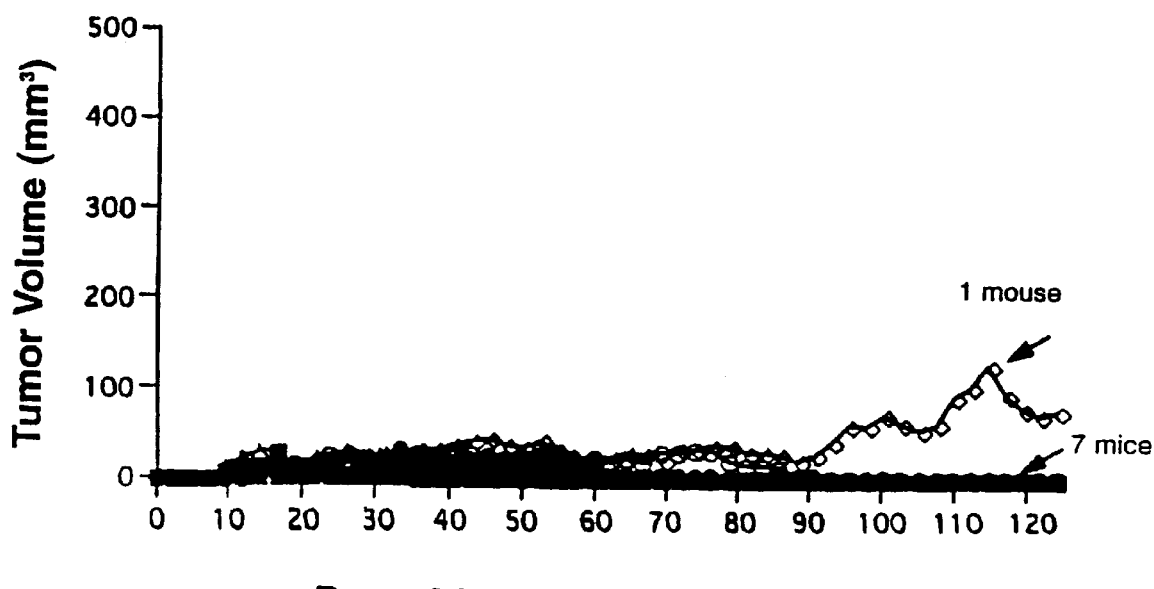
FIG. 2D is a graph depicting the progression in SCID mice of a human xenograft consisting of breast cancer cells (MCF-7), following pretreatment with unconjugated anti-endoglin mAb (K4-2C10) and then subsequent administration of the immunoconjugate (K4-2C10-dgRA conjugate).

Palpable tumor started appearing 1 to 2 weeks post tumor inoculation for all four groups of mice. However, there were remarkable differences in tumor growth between the immunoconjugate-treated groups and the groups not receiving immunoconjugate treatment. As shown in FIG. 2A, tumors in all of the untreated mice continued to grow for as long as the mice were followed. As shown in FIG. 2B, unconjugated mAb K4-2C10 alone was not significantly effective in inhibiting tumor growth. In contrast, and as shown in FIGS. 2C & 2D, the groups of mice treated with the immunoconjugate (K4-2C10-dgRA conjugate) showed significant tumor regression. Tumors in all eight of the mice treated with immunoconjugate alone (group 3) resulted in complete tumor regression, and the regression continued for as long as the mice were followed (125 days). Thus, based on these results, a first embodiment for effectively delivering antiangiogenic therapy is by administering the immunoconjugate alone. Tumors in seven of eight (87.5%) of the mice pretreated with unconjugated mAb and then treated with the immunoconjugate (group 4) regressed completely, and the regression continued for as long as the mice were followed (125 days post tumor inoculation). Thus, based on these results, a second embodiment for effectively delivering antiangiogenic therapy is by administering unconjugated mAb followed by administering the immunoconjugate. Statistical analysis of the data was carried out using Student's t-test, and Fisher's exact test. In each test, the differences between the immunoconjugate-treated groups (groups 3 and 4) and the control group (group 1) were statistically significant ($p < 0.001$).

These results indicate that antiangiogenic therapy with the immunoconjugate, comprised of an anti-endoglin mAb according to the present invention and coupled to an anti-tumor agent, is highly effective in exerting curative antitumor effects in a mouse model of human disease without overt side effects. The antiangiogenic therapy according to either the first or second embodiments of the present invention was effective in inducing complete regression of human solid tumor in the treated SCID mice. Having illustrated a maximum tolerated dose, and therapeutic regimen, for the immunoconjugate in the animal model for human disease using an anti-endoglin mAb according to the present invention, scaling up from the mouse model to humans may be performed using methods known to those skilled in the art (see, e.g., Baxter et al., 1995, supra). Additionally, this information, and by comparing the immunoreactivity (e.g., affinity and avidity) for endoglin on human endothelial cells of such a mAb with the immunoreactivity demonstrated by an anti-endoglin mAb that recognizes only human vascular endothelial cells, facilitates a method of using immunoconjugates comprising anti-endoglin mAbs that recognize only human vascular endothelial cells. A comparison of such immunoreactivities can be achieved by methods described herein (e.g. cellular RIA), and known in the art.

In a second therapeutic protocol, four groups of 6–8 SCID mice inoculated subcutaneously with $8 \times 10^6$ MCF-7 breast cancer cells/mouse were included. Using the methods according to the first protocol, a first group was untreated (control). A second group was treated by i.v. administration of unconjugated (free) mAb K4-2C10, but on days 3, 4, and 5 post tumor inoculation. A third group was treated by i.v. administration with the K4-2C10-dgRA conjugate, but on days 3, 4, and 5 post tumor inoculation. A fourth group was treated by i.v. administration of unconjugated (free) mAb K4-2C10 (50 µg; 1 day post tumor inoculation) followed by i.v. administration with the K4-2C10-dgRA conjugate on days 3, 4, and 5 post tumor inoculation. The mice were evaluated using the methods and parameters according to the first therapeutic protocol.

Figure 3A:
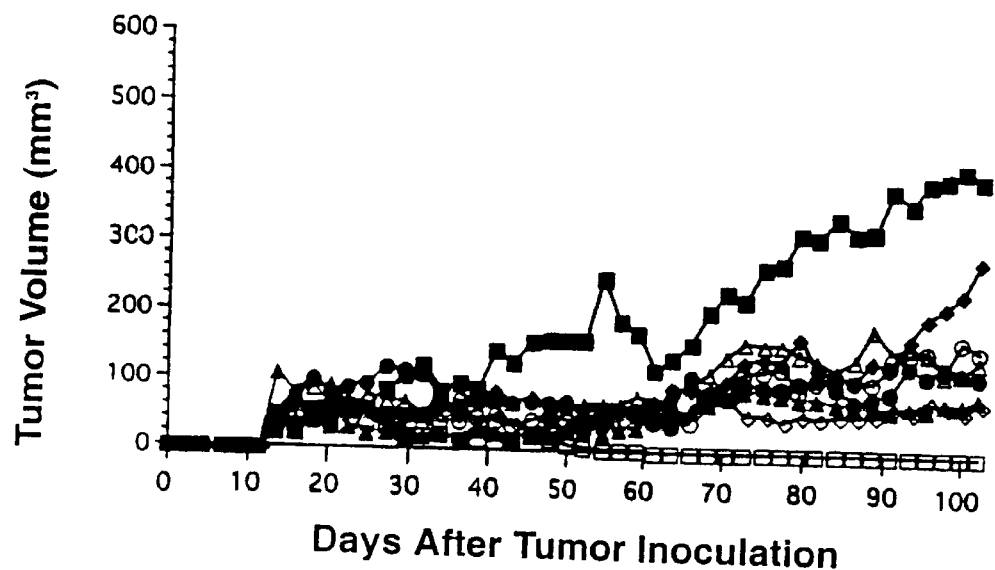
FIG. 3A is a graph depicting the progression in SCID mice of a human xenograft consisting of breast cancer cells (MCF-7).
Figure 3B:
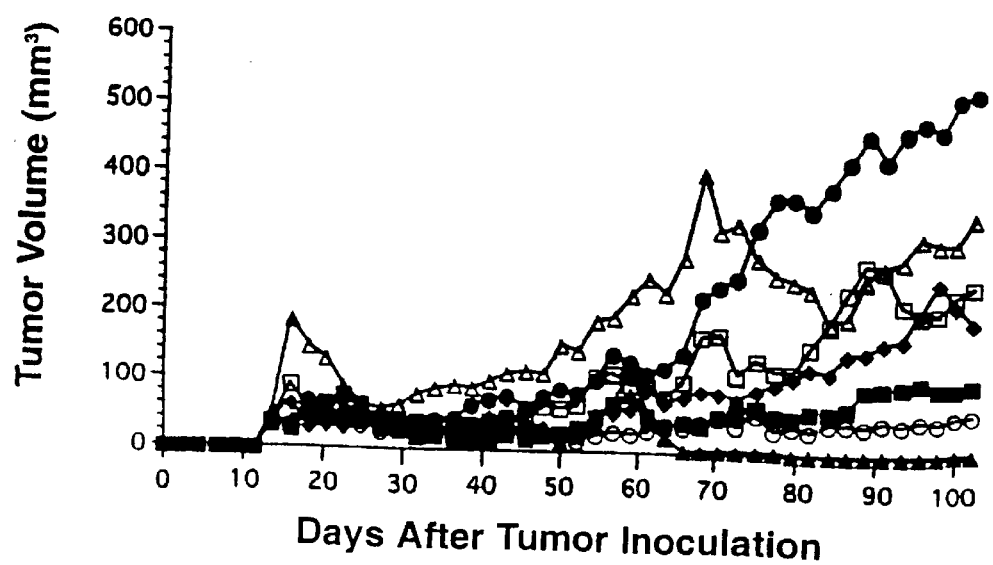
FIG. 3B is a graph depicting the progression in SCID mice of a human xenograft consisting of breast cancer cells (MCF-7), following treatment with unconjugated mAb K4-2C10.
Figure 3C:
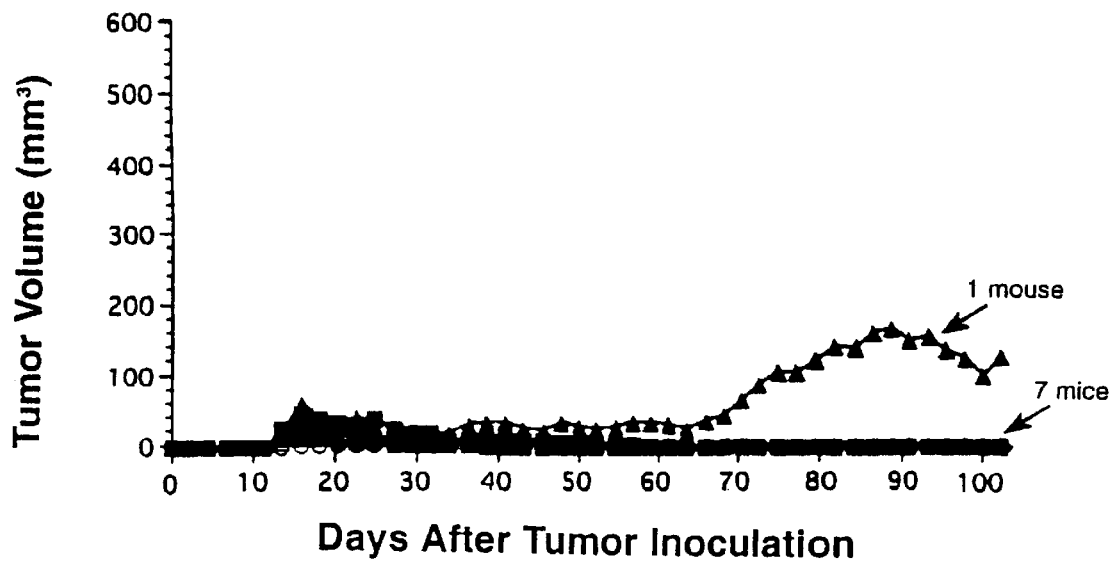
FIG. 3C is a graph depicting the progression in SCID mice of a human xenograft consisting of breast cancer cells (MCF-7), following treatment with an immunoconjugate (K4-2C10-dgRA conjugate).
Figure 3D:
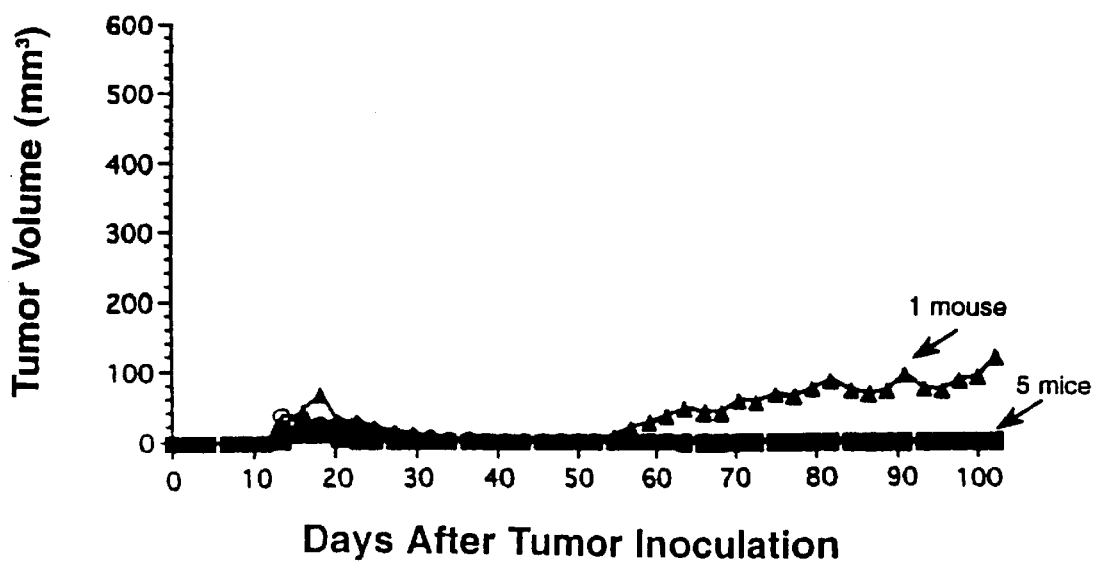
FIG. 3D is a graph depicting the progression in SCID mice of a human xenograft consisting of breast cancer cells (MCF-7), following pretreatment with unconjugated anti-endoglin mAb and then subsequent administration of the immunoconjugate (K4-2C10-dgRA conjugate).
Figure 4A:
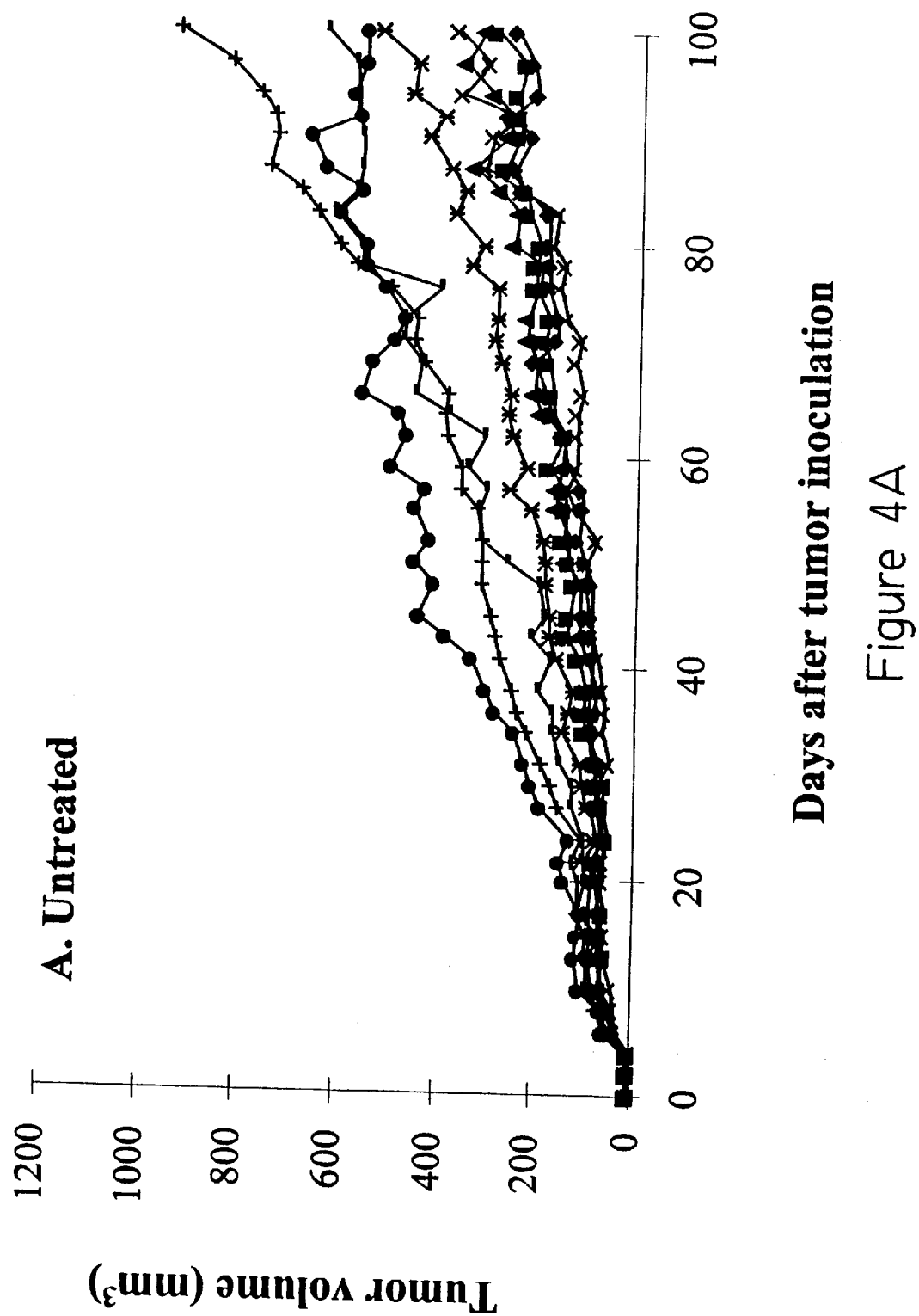
FIG. 4A is a graph depicting the progression in SCID mice of a human xenograft consisting of breast cancer cells (MCF-7), with each curve representing a different mouse.
Figure 4B:
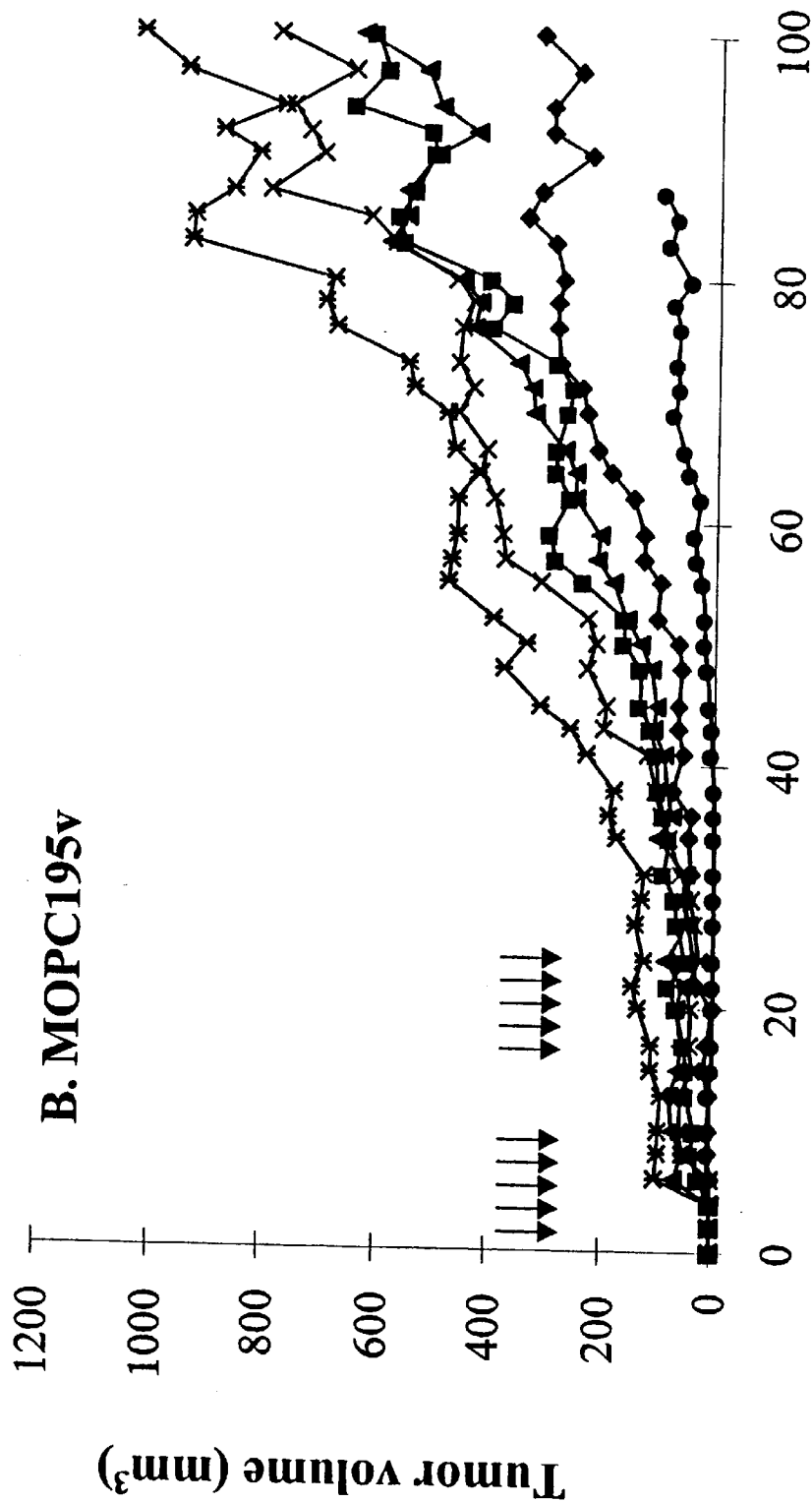
FIG. 4B is a graph depicting the progression in SCID mice of a human xenograft consisting of breast cancer cells (MCF-7), following treatment by injections of a control mouse IgG (MOPC 195 variant). Each of the injections is indicated by an arrow.
Figure 4C:
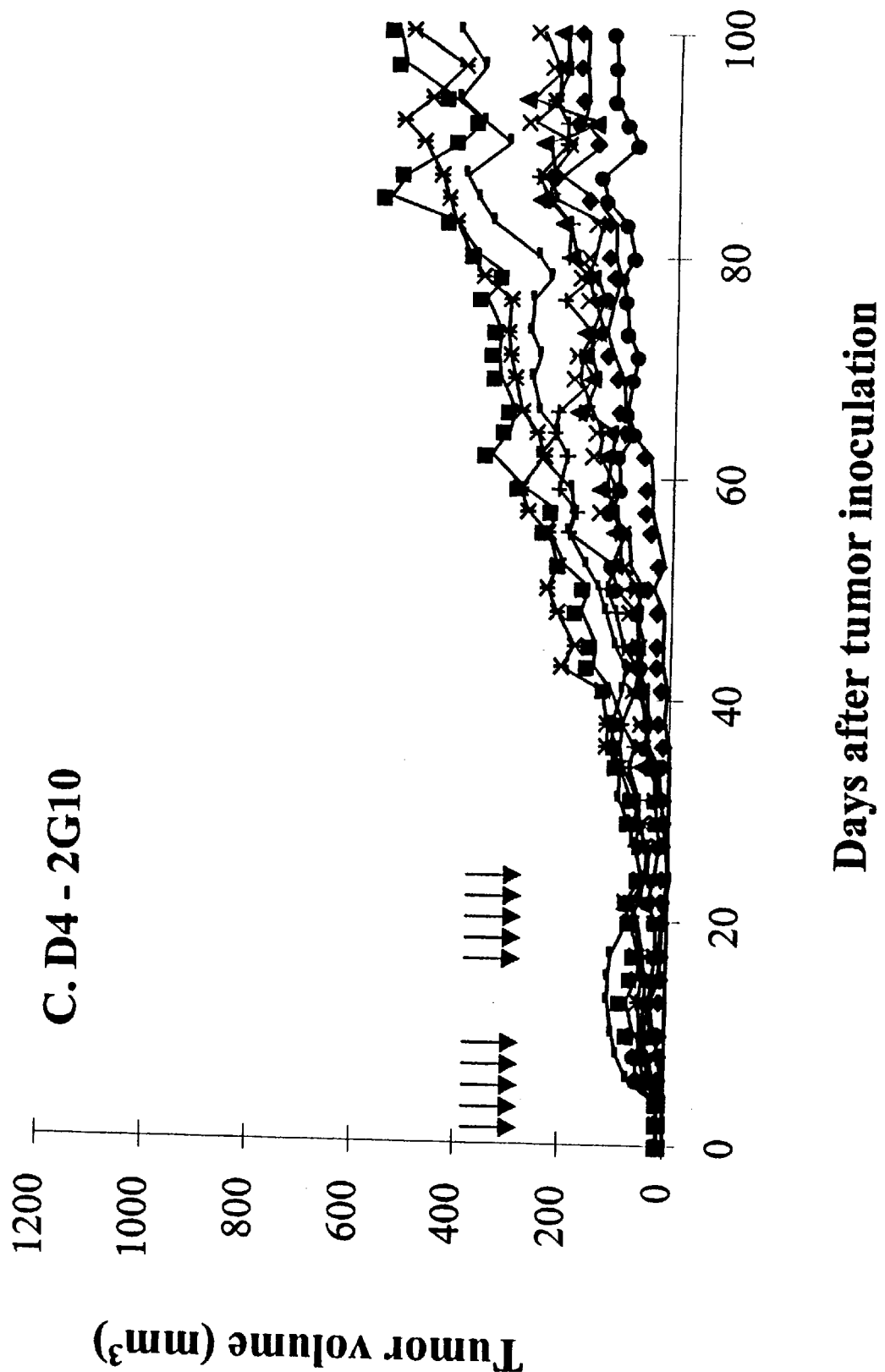
FIG. 4C is a graph depicting the progression in SCID mice of a human xenograft consisting of breast cancer cells (MCF-7), following treatment by injections of unconjugated mAb D4-2G10.
Figure 4D:
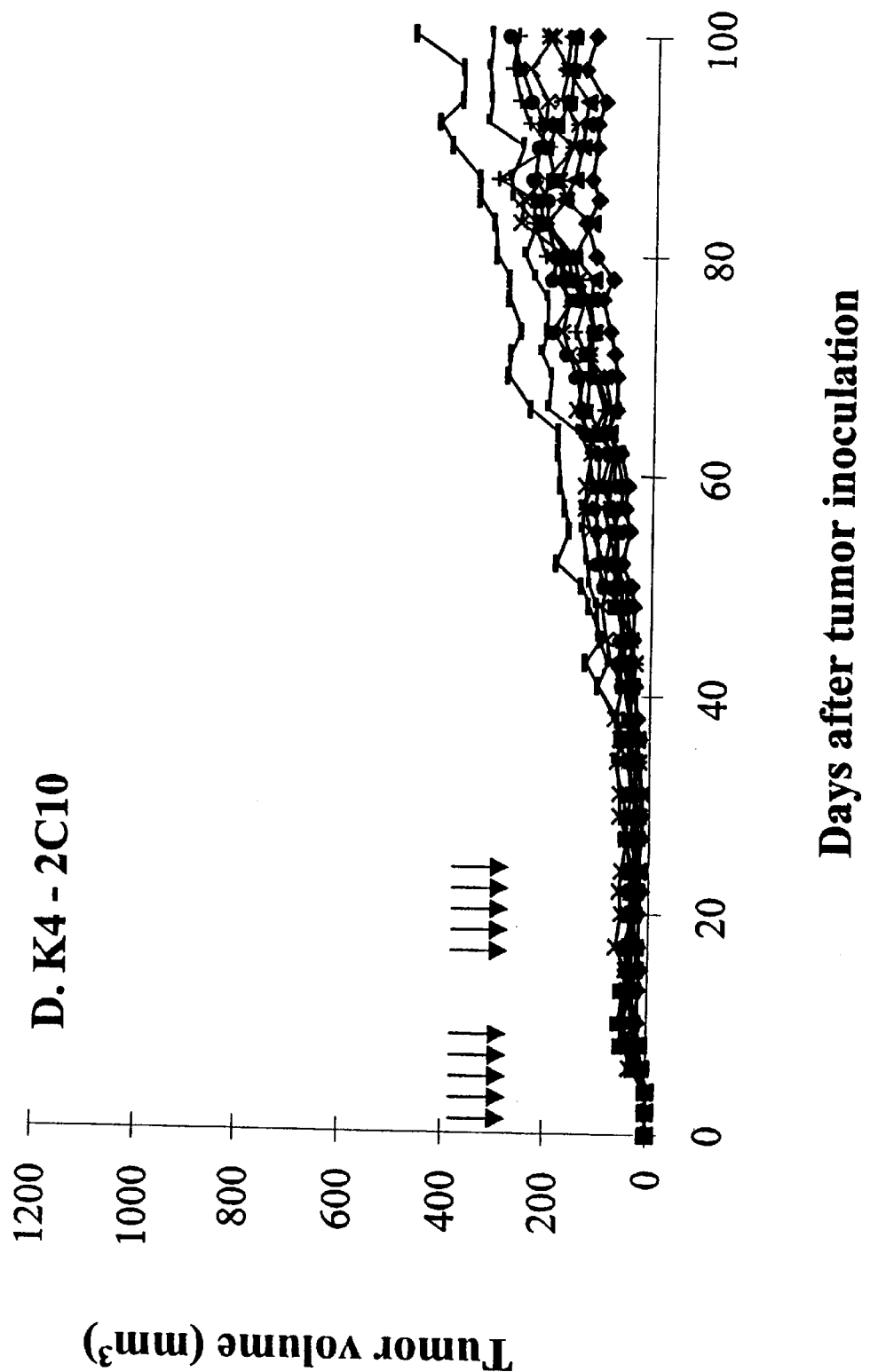
FIG. 4D is a graph depicting the progression in SCID mice of a human xenograft consisting of breast cancer cells (MCF-7), following treatment by injections of unconjugated mAb K4-2C10.
Figure 4E:
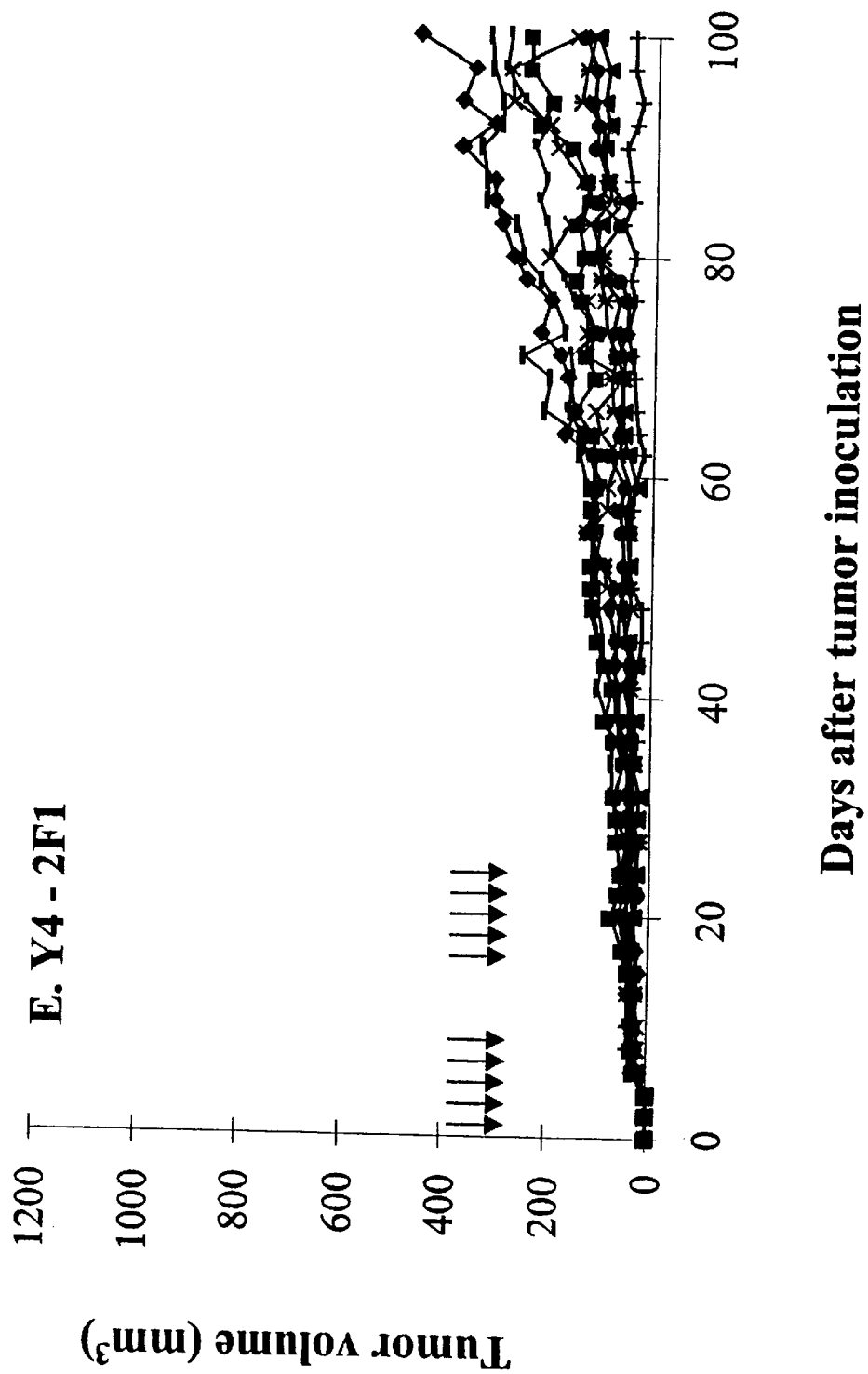
FIG. 4E is a graph depicting the progression in SCID mice of a human xenograft consisting of breast cancer cells (MCF-7), following treatment by injections of unconjugated mAb Y4-2F1.
Figure 4F:
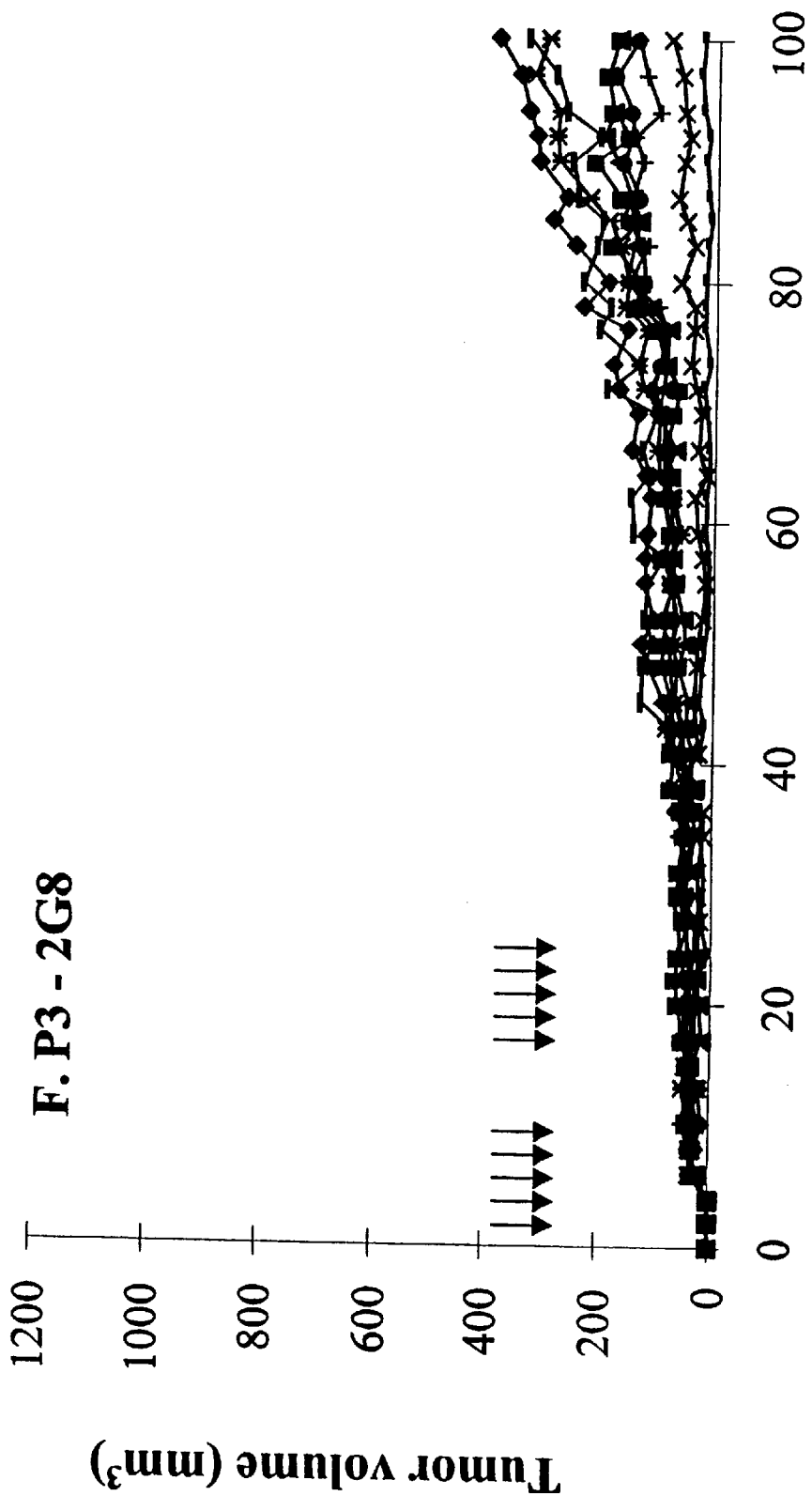
FIG. 4F is a graph depicting the progression in SCID mice of a human xenograft consisting of breast cancer cells (MCF-7), following treatment by injections of unconjugated mAb P3-2G8.

As shown in FIG. 3A, tumors in all but one of the eight group 1 (untreated) mice continued to grow for as long as the mice were followed. As shown in FIG. 3B, unconjugated mAb K4-2C10 alone was not significantly effective in inhibiting tumor growth. In contrast, and as shown in FIGS. 3C & 3D, the groups of mice treated with the immunoconjugate (K4-2C10-dgRA conjugate) showed significant tumor regression. Tumors in seven of eight (87.5%) of the mice treated with the immunoconjugate only (group 3) regressed completely, and the regression continued for as long as the mice were followed (105 days post tumor inoculation), as shown in FIG. 3C. As shown in FIG. 3D, tumors in 5 of the 6 mice pretreated with unconjugated anti-endoglin mAb followed by administration of the immunoconjugate (group 4) regressed completely, and the regression continued for as long as the mice were followed (105 days post tumor inoculation). The results of the second therapeutic protocol are highly consistent with the results of the first therapeutic protocol; i.e., antiangiogenic therapy using the anti-endoglin mAb conjugate is effective in inducing lasting complete regression of human solid tumors without overt side effects.

The highly effective in vivo antitumor effect of the immunoconjugate is an unexpected result for the following reasons. First, mAb K4-2C10 reacts only weakly with mouse endothelial cells and K4-2C10-dgRA conjugate is only weakly cytotoxic to mouse endothelial cells (as compared to human endothelial cells, and particularly to proliferating human endothelial cells). Furthermore, a relatively small amount (corresponding to 24% of $LD_{50}$ dose) of the immunoconjugate was administered i.v. In the conventional tumor-cell targeted therapy, even highly potent antitumor immunotoxins have rarely shown such strong in vivo antitumor effects when a small amount of the agent was administered i.v. As taught in the present invention, the immunoconjugate is selectively targeted to vasculature rather than being directed to the tumor per se. However, unlike other reported attempts of using targeting agents against tumor angiogenesis (as reviewed in Folkman, 1995, supra; Sipos et al., 1994, *Ann. NY Acad. Sci.* 732:263–272; Hawkins, 1995, *Curr. Opin. Oncol.* 7:90–93), using anti-human endoglin mAb in immunoconjugates according to the present invention can exert long-lasting and practically curative antitumor effects.

4. In Vitro Suppressive Activity of Unconjugated Monoclonal Antibodies

In a third embodiment, the uconjugated mAbs are used for antiangiogenic therapy. The in vitro suppressive activity of unconjugated anti-endoglin mAbs was evaluated by using a $^3$H-thymidine incorporation assay (Seon et al., 1997, *Clin. Cancer Res.*, 3:1031–1044). In this assay, the inhibitory activity of unconjugated anti-endoglin mAbs against proliferation of human umbilical vein endothelial cells (HUVEC) was measured. Briefly, HUVEC were distributed, in triplicate, into wells of flat-bottomed 96-well microtiter plates at $5\times10^3$ cells/well. Varying amounts of an mAb, isotype-matched control IgG, or medium (control) were added to wells, and the plates were incubated for 24 hours at 37° C. in a 5% $CO_2$ incubator. The cells were pulsed with 1 $\mu$Ci/well [$^3$H]thymidine for 20 hours and treated with trypsin-EDTA (0.05% trypsin/0.53 mMEDTA) for 15 min at 37° C. to detach the cells from the plate wells. The detached cells were harvested on glass fiber filters using an automatic harvester (TOMTEC harvester 96, Wallace, Inc., Gaithersburg, Md.). The radioactivity was determined in a liquid scintillation and luminiscence counter (Trilux 1450 MicroBeta). K4-2C10, Y4-2F1 and P3-2G8 inhibited the $^3$H-thymidine incoporation into HUVEC by 19.7, 16.3, and 21.3% respectively, after incubation for 24 hours, while an isotype-matched control IgG (MOPC 195 variant, IgG1-K) showed no significant inhibition.

5. Maximum Tolerated Dose of Unconjugated Monoclonal Antibody in Mice

Groups of four normal female BALB/cmice (7-weeks old) were injected intravenously (via the tail vein) with Y4-2F1 mAb at doses of 0.2, 0.4, 0.8, 1.6, 3.2, and 6.4 mg/mouse. Mice were weighed prior to injection and daily thereafter and were observed for morbidity and mortality for 2 weeks. No significant toxic effect was detected at any doses. The average body weight of the four mice that received the highest dose (i.e. 6.4 mg) was 18.58±0.66g. Therefore, the maximum tolerated doe of mAb SN6j is higher than 0.344 mg/g body weight of mice. This lack of toxicity of the unconjugated mAb SN6j is in contrast with the significant toxicity of the deglycosylated ricin A-chain (dgRA) conjugate of SN6j of which $LD_{50}$ (50% of lethal dose) was 0.0166mg/g body weight (Matsuno et al., 1999, 5:371–382). $LD_{50}$ values of SN6f-dgRA and SN6k-dgRA were 0.0148 and 0.0165 mg/g body weight (Seon et al., 1997, supra; Matsuno et al., 1999, supra).

6. Antiangiogenic Therapy Using Unconjugated Monoclonal Antibodies

Unconjugated mAbs, D4-2G10, K4-2C10, Y4-2F1 and P3-2G8 were used to show the antiangiogenic therapy according to the present invention.

A. SCID mice with human xenografts comprising MCF-7 human breast cancer cells were used as a model for evaluation of antiangiogenic therapy using unconjugated antibodies. The model was prepared as described above in 3B.

B. In this embodiment, the antiangiogenic therapy comprising administration of each of the four cross-reactive anti-endoglin mAbs was tested in the SCID mouse-MCF-7 xenograft model. A first group of 8 SCID mice that were inoculated subcutaneously with $8\times10^6$ MCF-7 cells/mouse were untreated (control). A second group of 6 SCID mice that were inoculated subcutaneously with $8\times10^6$ MCF-7 cells/mouse were treated by i.v. administration of 200 ug of a control mouse IgG (MOPC 195 variant). A third group of 8 SCID mice that were inoculated subcutaneously with $8\times10^6$ MCF-7 cells/mouse were treated by i.v. administration of 200 ug of D4-2G10. A fourth group of 8 SCID mice that were inoculated subcutaneously with $8\times10^6$ MCF-7 cells/mouse were treated by i.v. administration of 200 ug of mAb K4-2C10. A fifth group of 8 SCID mice that were inoculated subcutaneously with $8\times10^6$ MCF-7 cells/mouse were treated by i.v. administration of 200 ug of mAb Y4-2F1. A sixth group of 8 SCID mice that were inoculated subcutaneously with $8\times10^6$ MCF-7 cells/mouse were treated by i.v. administration of 200 ug of mAb P3-2G8. The therapy was started on day 1 (one day after tumor inoculation) as indicated by arrows in FIGS. 4A–4F. The total dosage used was much less that the maximum tolerated dose of unconjugated mAb.

During the treatment, mice were monitored daily for tumor size and for morbidity, and weight of the mice was measured twice each week. Tumor volumes were estimated, and statistical analysis carried out, as described above in 3C. The analysis was performed for points at 10-day intervals, i.e., 10,20,30,40,50,60,70,80,90 and 100. K4-2C10, Y4-2F1 and P3-2G8 showed statistically significant antitumor efficacy during days 30–90 (p<0.02). Antitumor efficacy of D4-2G10 was significant only during days 30–40 (p<0.05). The results demonstrate significant antitumor efficacy of free (unconjugated) anti-endoglin antibodies. No significant side effects or weight loss was detected for treated mice.

Figure 5:
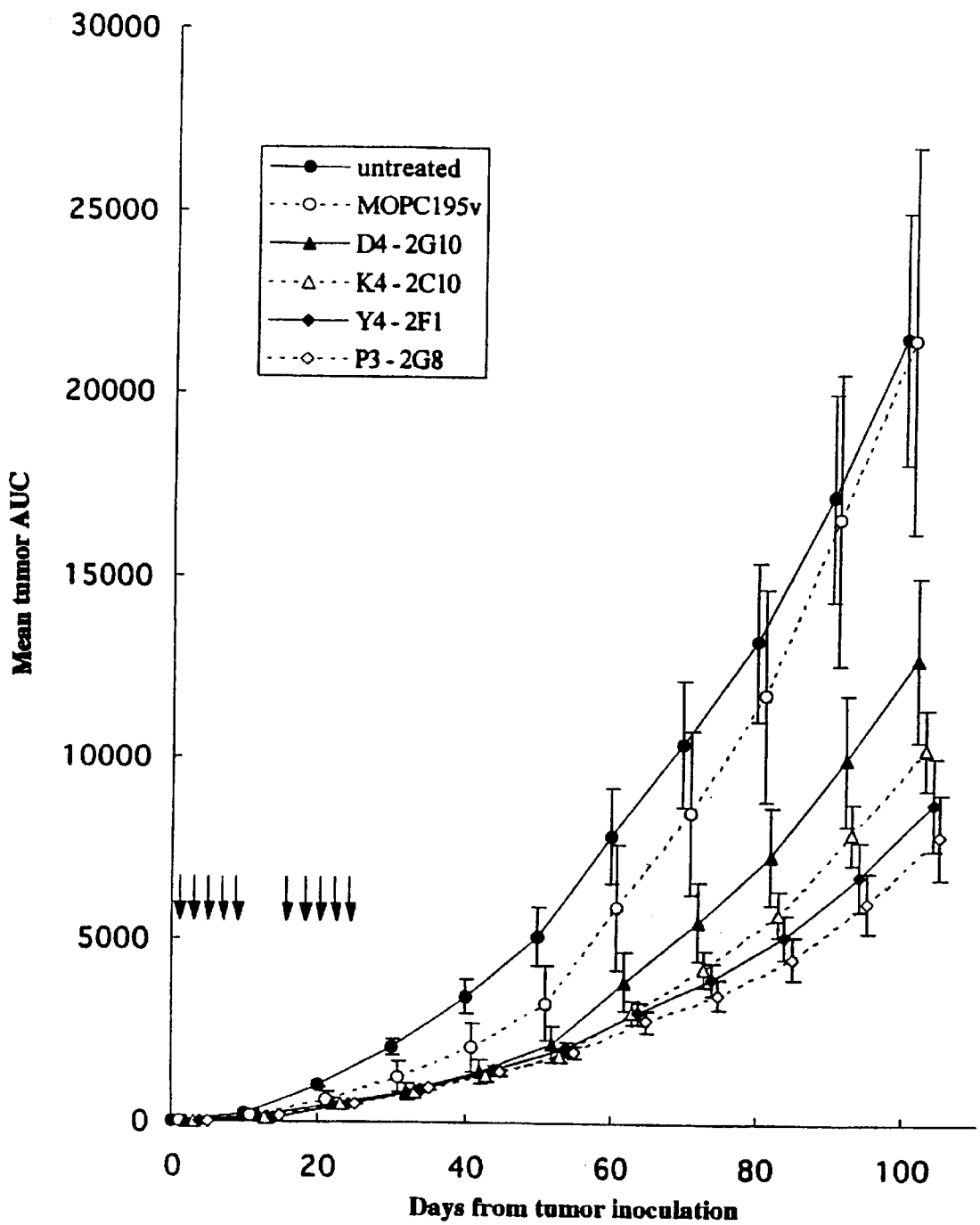
FIG. 5 is a graph depicting the progression in SCID mice of MCF-7 breast cancer cells as expressed by the area under the tumor growth curve, following treatment by injections of a control IgG (MOPC-195 variant), unconjugated mAb D4-2G10, unconjugated mAb K4-2C10, unconjugated mAb Y4-2F1 or unconjugated mAb P3-2G8, with each curve representing an average of different groups.

To evaluate cumulative antitumor efficacy of the treatment, the area under the tumor growth curve (tumor AUC) was compared between groups. The results are presented in FIG. 5. The results of FIG. 5 support the above conclusions drawn from the results of FIGS. 4A–F.

C. In additional tests, human skin/SCID mouse chimeras with human tumor grafts comprising MFC-7 human breast cancer cells was used as a model for evaluation of antiangiogenic therapy comprising administration of unconjugated mAb. To produce this model, fresh human neonatal foreskins (circumcized tissues) were obtained from the Cooperative Human Tissue Network (CHTN), University of Pennsylvania Medical Center, and stored in sterile RPMI 1640 media supplemented with 5% fetal bovine serum (FBS) and 1% gentamicin. The tissues were used for grafting on the same day as received. The grafting into SCID mice was performed essentially as described by Brooks et al., (1995, J. Clin. Invest., 96:1815–1822) and Juhasz et al., (1993, Am. J. Pathol., 143:528–537). Briefly, female SCID mice (6 weeks old) were anesthetized and a section of skin (approximately 2 $cm^2$) was surgically removed. A precut section of fresh full thickness human neonatal foreskin was sutured into place. The grafts were bandaged securely for 2 weeks to allow healing. Grafted human foreskin formed stable skin in 81 or 83 SCID mice (97.6%) in the present studies. MCF-7 human breast cancer cells ($8\times10^6$ cells/mouse) were inoculated intradermally (i.d.) Into the grafted human skins 6 to 7 weeks after the skins were grafted and after the graft healed completely. Blood vessels formed in the tumors in the grafted human skins consist of both human and mouse vessels (Kusaka et al., 1999, Proc. Am. Assoc. Cancer Res., 40:68). This is in contrast to MCF-7 tumor grown in mouse skins in which blood vessels formed in the tumors consist of mouse vessels only.

Figure 6A:
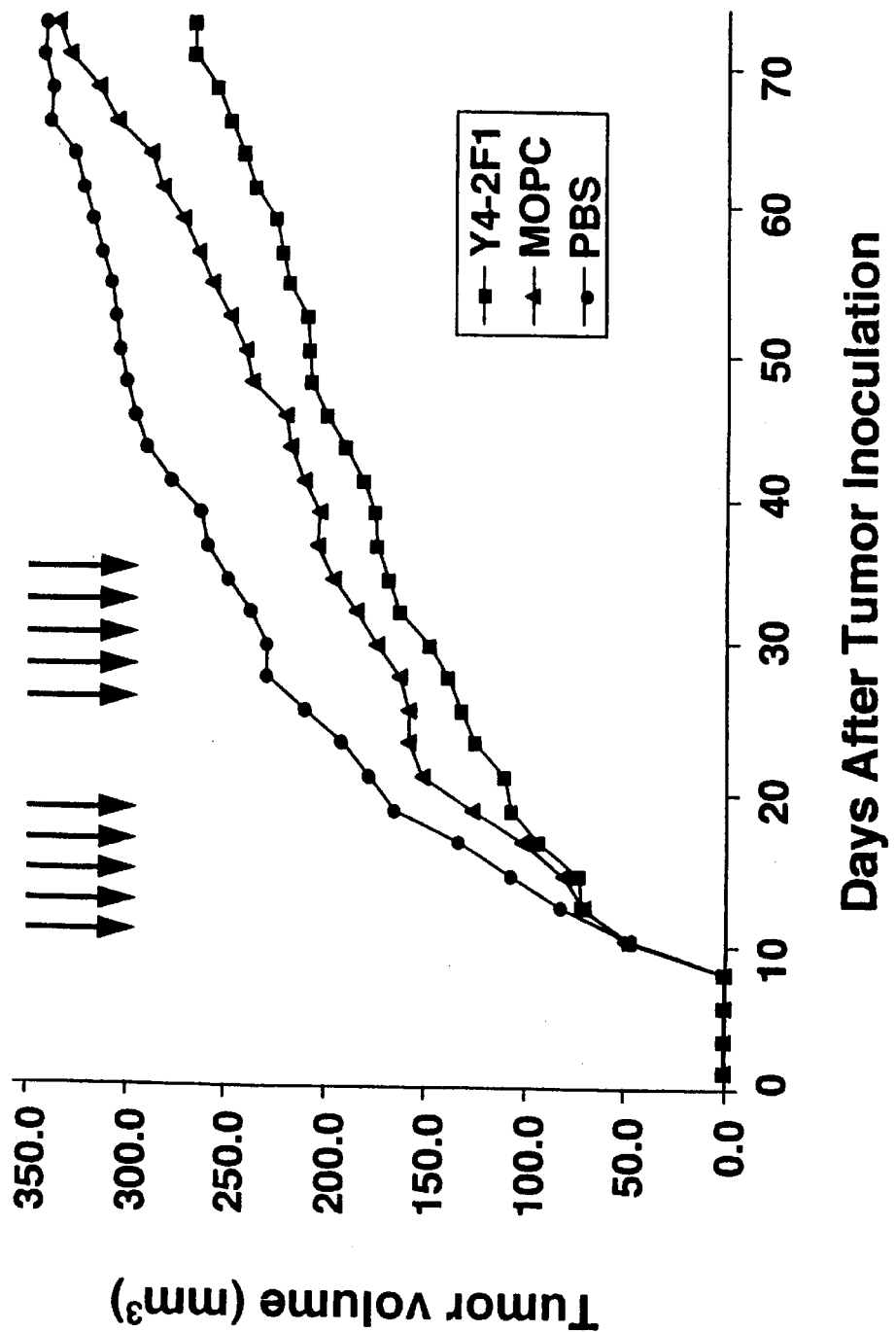
FIG. 6A is a graph depicting the progression of MCF-7 human breast cancer in human skin/SCID mouse chimeras, following treatment by injections of 200 µg/dose/mouse of unconjugated mAb Y4-2F1, 200 mg/dose/mouse of an isotype-matched control IgG (MOPC-195 variant), or PBS (control), with each curve representing an average of different groups.

D. The antiagiogenic therapy according to the present invention was tested in the human skin/SCID mouse chimera models bearing MCF-7 human breast tumors. Human skin/SCID mouse chimeras inoculated with NCF-7 cells ($8\times10^6$ cells/mouse) were left untreated until palpable distinct tumors (approximately 5 mm in diameter) appeared. In the first set of experiments, a first group of 4 human skin/SCID mouse chimeras that bore palpable distinct tumors of MCF-7 were treated by i.v. administration with PBS (control). A second group of 5 human skin/SCID mouse chimeras that bore palpable distinct tumors of MCF-7 were treated by i.v. administration with 200 ug/mouse of an isotype-matched control IgG (MOPC 195 variant; IgG1-K). A third group of 5 human skin/SCID mouse chimeras that bore palpable distinct tumors of MCF-7 were treated by i.v. administration with 200 ug/mouse of unconjugated mAb Y4-2F1. The therapy was repeated four times at two-day intervals. Another cycle of therapy was started one week later and repeated four times at two-day intervals (individual injections are indicated by vertical arrows in FIG. 6A).

Figure 6B:
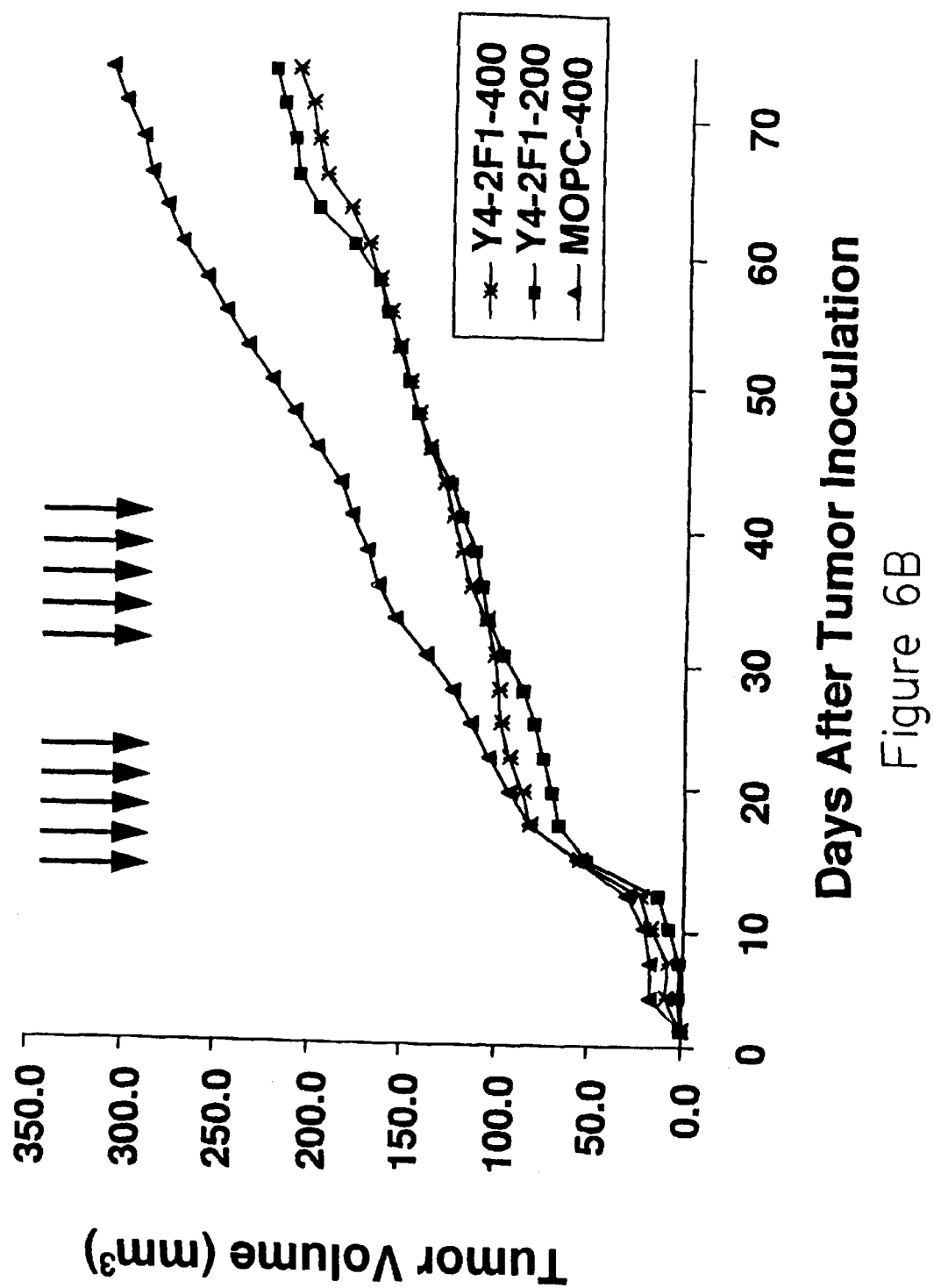
FIG. 6B is a graph depicting the progression of MCF-7 human breast cancer in human skin/SCID mouse chimeras, following treatment by injections of 400 ug/dose/mouse of unconjugated mAb Y4-2F1, 200 ug/dose/mouse of unconjugated mAb Y4-2F1, or 400 ug/dose/mouse of an isotope-matched control IgG (MOPC 195 variant; IgG1-k), with each curve representing an average of different groups.

In the second set of experiments, a first group of five human skin/SCID mouse chimeras that bore palpable distinct tumors of MCF-7 was treated by i.v. administration with 400 ug/mouse of an isotpye-matched control IgG (MOPC 195 variant). A second group of 6 human skin/SCID mouse chimeras that bore palpable distinct tumors of MCF-7 was treated by i.v. administration with 400 ug/mouse of unconjugated mAb Y4-2F1. A third group of 6 human skin/SCID mouse chimeras that bore palpable distinct tumors of MCF-7 was treated by i.v. administration with 200 ug/mouse of unconjugated mAb Y4-2F1. The therapy was repeated four times at two-day intervals. Another cycle of therapy was started one week later and repeated four times at two-day intervals (individual injections are indicated by vertical arrows in FIG. 6B). During treatment, the mice were monitored daily for tumor size and for morbidity, and weight of the mice was measured twice each week. Tumor volumes were estimated as described above in 3C. The results show significant antitumor efficacy for unconjugated mAb Y4-2F1. No significant side effects or weight loss was detected for treated mice.

These results indicate that antiangiogenic therapy with the unconjugated anti-endoglin mAbs is effective in exerting antitumor effects in a mouse model of human disease and in a human skin/mouse chimera model of human disease without overt side effects. As demonstrated herein, the antiangiogenic therapy was effective in suppressing human solid tumors in the treated SCID mice and in the treated human skin/SCID mouse chimeras. Having illustrated a maximum dose and therapeutic regimen for the mAb in the animal models for human disease using an anti-endoglin mAb according to the present invention, scaling up from the mouse models to humans may be performed using methods known to those skilled in the art (see Baxter et al., 1995, supra). Additionally, this information, and comparing the immunoreactivity for endoglin on human endothelial cells of such a mAb with the immunoreactivity demonstrated by anti-endoglin mAbs that recognize only human vascular endothelial cells, facilitates a method of using anti-endoglin mAbs that recognize only human vascular endothelial cells.

EXAMPLE 4

In Example 3 were illustrated three embodiments of a method according to the present invention for targeting therapies against tumor vasculature or the excessive vascularization present in angiogenesis-associated diseases. Using the method according to the first embodiment, it was demonstrated that an immunoconjugate comprising an anti-endoglin mAb according to the present invention and coupled to an antitumor agent will destroy tumor-associated vasculature by selectively reacting with proliferating endothelial cells of tumor-associated neovasculature and destroying existing tumor-associated blood vessels, thereby preventing tumor-associated angiogenesis from developing and preventing pre-formed tumors from growing (see, e.g., FIGS. 2C and 3C). In Example 3 is illustrated a second embodiment of a method of according to the present invention for antiangiogenic therapy. According to the second embodiment, utilized is an immunoconjugate produced using an anti-endoglin mAb according to the present invention, or a fragment thereof, coupled to either at least one antitumor agent, or an angiogenesis inhibitor in forming the immunoconjugate. However, in this second embodiment of antiangiogenic therapy, the tumor-bearing host or the host having excessive vascularization due to an angiogenesis-associated disease is pretreated with unconjugated anti-endoglin mAb according to the present invention, or a fragment thereof (e.g. $F(ab')_2$). The rationale for pretreatment prior to administration of the immunoconjugate is that the pretreatment with an unconjugated anti-endoglin mAb recognizing the same epitope on the endoglin as the immunoconjugate may further enhance the selectivity of the immunoconjugate for the target vasculature. For example, endothelial cell turnover in normal quiescent vasculature is very slow. In contrast, the endothelial cells found in the tumor-associated neovasculature or in the excessive vascularization present in angiogenesis-associated diseases undergo rapid proliferation during spurts of angiogenesis (see, e.g. Folkman et al., 1992, J. Biol. Chem. 267:10931–10934). Therefore, pretreatment of the host with unconjugated anti-endoglin mAb, or a fragment thereof, may be able to mask (precoat) the weak binding sites on quiescent endothelial cells in the normal (undiseased) tissues, while high amounts of newly generated binding sites on the proliferating endothelial cells found in angiogenesis are then available for binding by a subsequent administration of the immunoconjugate. Precoating normal tissue before administration of the immuno-conjugate may reduce undesirable side effects of the administered immunoconjugate potentially caused by the immunoconjugate reacting weakly with normal tissue. Additionally, the precoating step may enhance the antiangiogenic efficacy of the immunoconjugate because of the more efficient delivery of the systemically administered immunoconjugate to the target vasculature. As illustrated in FIGS. 2D and 3D, vasculature (tumor-associated neovasculature, or excessive vascularization present in angiogenesis-associated diseases) can be effectively targeted by systemic administration of the immunoconjugate after the host was administered a precoating of unconjugated anti-endoglin mAb. Thus, i.v. administration of unconjugated anti-endoglin mAb into patients as a precoating step, followed by i.v. administration with anti-endoglin immunoconjugate, is a novel and effective approach to antiangiogenic therapy.

In the third embodiment, the mAbs can be used without being conjugated to agents.

EXAMPLE 5

Illustrated and detailed in Examples 3 and 4 were three embodiments for a method according to the present invention for targeting therapies against tumor vasculature, or the excessive vascularization present in angiogenesis-associated diseases, in the SCID mouse-human xenograft model. Another mouse model of human angiogenesis-associated disease was utilized to demonstrate the antiangiogenic therapy using the anti-endoglin mAbs and methods of use according to the present invention. Antiangiogenic activity of the immunoconjugate, K4-2C10-dgRA, was tested by the dorsal air sac method (see, e.g., Asano et al., 1995, *Cancer Res.* 55: 5296–5301), an assay for in vivo angiogenesis. Briefly, $1 \times 10^7$ HT1080 human tumor cells were suspended in PBS and then placed into a plastic chamber (14 mm in diameter) which was sealed at each chamber end with a cellulose membrane filter (0.45 µm pore size). A chamber, so prepared, was implanted into a dorsal air sac of each of several female BALB/c mice. One group of mice containing the implants was untreated as a positive control of angiogenesis. A second group of mice containing the implants was treated by i.v. administration with unconjugated mAb K4-2C10 (17 µg/0.2 ml) 2 hours, 24 hours and 48 hours post chamber implantation. A third group of mice containing the implants was treated by i.v. administration with immunoconjugate, K4-2C10-dgRA (20 µg/0.2 ml) 2 hours, 24 hours and 48 hours post chamber implantation. A fourth group of mice was implanted with chambers only containing PBS (without any tumor cells) and untreated as a negative control of angiogenesis. On day 4, the mice of each group were analyzed for the formation of new blood vessels (angiogenesis) in subcutaneous regions. Mice of the positive control group (group 1) showed strong induction of angiogenesis as characterized by numerous new microvessels, and considerably enlarged pre-existing small vessels. Treatment of mice with the immunoconjugate resulted in significant suppresion of angiogenesis, whereas mice treated with unconjugated mAb K4-2C10 showed much less inhibition of angiogenesis. These results further support the administration of anti-endoglin immunoconjugate as a novel and effective approach to antiangiogenic therapy.

This mouse model was also used to further illustrate the antiangiogenic effects of unconjugated anti-endoglin mAb K4-2C10. Briefly, $1.6 \times 10^7$ MCF-7 human tumor cells in 0.2 ml PBS were placed into a chamber (Millipore, 14 mm in diameter) which was sealed at each end with cellulose membrane filter (0.45 µm pore size). This chamber was implanted into a dorsal air sac of each of several female BALB/c mice; the dorsal air sac was generated by injecting 7 ml air. Two groups of three mice each implanted with a chamber containing MCF-7 cells were untreated (angiogenesis positive control), or treated by i.v. administration with unconjugated mAb K4-2C10 (34 ug/0.2 ml) at 1, 2 and 3 days after chamber implantation. Another group, the third group, of three mice was implanted with a chamber containing PBS (angiogenesis-negative control). The mice were sacrificed on day 4 and blood vessels in the excised skin were examined under a microscope. Mice of the positive control group (group 1) showed strong induction of angiogenesis as characterized by numerous new microvessels. Treatment of mice with unconjugated mAb K4-2C10 resulted in substantial suppression of angiogenesis. These results further support the administration of unconjugated anti-endoglin mAbs as a novel and effective approach to antiangiogenic therapy.

EXAMPLE 6

In Examples 3 and 4 were illustrated in mouse models of human disease, various embodiments for a method of according to the present invention for targeting therapies against tumor vasculature or the excessive vascularization present in angiogenesis-associated diseases. Using the method according to these embodiments, it was demonstrated that unconjugated anti-endoglin mAb or an immunoconjugate comprising an anti-endoglin mAb according to the present invention and coupled to an antitumor agent will selectively react with, and destroy, proliferating endothelial cells of the targeted vasculature, thereby preventing the associated angiogenesis from developing. Further, precoating with unconjugated anti-endoglin mAb followed by administration of the immunoconjugate is also effective in antiangiogenic therapy.

One skilled in the art would appreciate that the antiangiogenic therapy (using an anti-endoglin mAb according to the present invention, and/or an anti-endoglin mAb that recognizes only human vascular endothelial cells) according to the embodiments presented herein, would need to be optimized for clinical use in humans. A physiological basis for scaling up the therapeutic agents comprising mAbs from a mouse model to humans is known to those skilled in the art (see, e.g., Baxter et al., 1995, supra). For example, the optimal timing for the subsequent administration of immunoconjugate after pretreatment with unconjugated anti-endoglin mAb, and the optimal molar ratio of unconjugated anti-endoglin mAb to immunoconjugate, may need to be determined for patients for tumor-associated neovasculature or the excessive vascularization present in angiogenesis-associated diseases. The optimal timing will be influenced by several factors such as the pharmacokinetics of the administered anti-endoglin mAb according to the present invention, or a fragment thereof. Also a factor is the rate of endocytosis/shedding of the mAb, or fragment thereof, bound to human endoglin on the surface of human endothelial cells. Pretreatment of patients with autologous or homologous anti-endoglin mAb may enhance the safety and efficacy of the clinical application of an anti-hEDG mAb immunoconjugate according to the method of the present invention.

In another embodiment of the antiangiogenic therapy according to the present invention, a human patient having an angiogenesis-associated disease such as diabetic retinopathy, chronic inflammatory diseases, rheumatoid arthritis, dermatitis, or psoriasis is treated with a therapeutic protocol of multiple administrations of an unconjugated antibody or an immunoconjugate according to the present invention. The immunoconjugate comprises an anti-human endoglin mAb according to the present invention, or a fragment thereof, (or alternatively, an anti-endoglin mAb, or a fragment thereof, that recognizes only human vascular endothelial cells) which is coupled to at least one angiogenesis inhibitor or to at least one cytotoxic agent (e.g., a toxin). The immunoconjugate may further comprise a pharmaceutically acceptable carrier medium. In a further embodiment, the human patient is pretreated with unconjugated anti-endoglin mAb (or a fragment thereof) followed by administration of an anti-hEDG mAb (or a fragment thereof) immunoconjugate according to the present invention. The unconjugated anti-endoglin mAb (or a fragment thereof) may further comprise a pharmaceutically acceptable carrier medium.

In a further embodiment of the antiangiogenic therapy according to the present invention, a human patient having a solid tumor, including angiosarcoma, breast carcinoma, cecum carcinoma, colon carcinoma, Hodgkins lymphoma, lymphoma, lung carcinoma, melanoma, osteosarcoma, ovarian carcinoma, parotid tumor, pharyngeal carcinoma, and rectosigmoid carcinoma, is treated with a therapeutic protocol of multiple administrations of an unconjugated antibody or an immunoconjugate according to the present invention. The immunoconjugate comprises an anti-human endoglin mAb according to the present invention, or a fragment thereof, (or alternatively, an anti-endoglin mAb, or fragment thereof, that recognizes human vascular endothelial cells and is not cross-reactive with murine endothelial cells) which is coupled to at least one angiogenesis inhibitor or to at least one antitumor agent. The immunoconjugate may further comprise a pharmaceutically acceptable carrier medium. In a further embodiment, the human patient is pretreated with unconjugated anti-endoglin mAb (or a fragment thereof) followed by administration of an anti-hEDG mAb (or a fragment thereof) immunoconjugate according the present invention. The unconjugated anti-endoglin mAb (or a fragment thereof) may further comprise a pharmaceutically acceptable carrier medium.

One of skill in the art would appreciate that depending on the angiogenesis inhibitor or antitumor agent used, the therapeutic protocol may require additional steps. For example, where the administered immunoconjugate comprises an anti-hEDG (or fragment thereof) conjugated to a photosensitizer (mostly porphyrins), a further step of irradiation with light of the targeted area is required.

EXAMPLE 7

In Examples 3–5 was demonstrated the administration of anti-endoglin immunoconjugate as a novel and effective approach to antiangiogenic therapy, wherein the anti-endoglin mAb is used to target therapies against tumor vasculature or the excessive vascularization present in angiogenesis-associated diseases. While the monoclonal antibody used to illustrate the effectiveness of antiangiogenic therapy according to the method of the present invention is a murine monoclonal antibody, it will be appreciated by those skilled in the art that such murine mAbs may be modified ("engineered") using techniques standard in the art (e.g., as reviewed by Adair, 1992, *Immunological Reviews* 130: 5–40, herein incorporated by reference).

For example, murine monoclonal antibodies may be made chimeric or "humanized" by replacing portions of the murine monoclonal antibody with the equivalent human sequence. In one embodiment, a chimeric antibody is constructed. The construction of chimeric antibodies is now a straightforward procedure (Adair, 1992, supra, at p. 13) in which the chimeric antibody is made by joining the murine variable region to a human constant region. Additionally, "humanized" antibodies may be made by joining the hypervariable regions of the murine monoclonal antibody to a constant region and portions of variable region (light chain and heavy chain) sequences of human immunoglobulins using one of several techniques known in the art (Adair, 1992, supra; Singer et al., 1993, *J. Immunol.* 150:2844–2857, herein incorporated by reference). Techniques for constructing chimeric antibodies (murine-human) of therapeutic potential have been described previously (see, e.g., Morrison et al., 1984, *Proc. Natl. Acad. Sci.* 81:6851–6855; Larrick et al., 1991, *Hum. Antibod. Hybridomas* 2:172–189; herein incorporated by reference). Thus, in one embodiment of the present invention, and using methods known in the art, the murine variable region of the anti-endoglin mAb according to the present invention is joined to a human constant region to form a chimeric anti-endoglin antibody having the same specificity as the anti-endoglin mAb. In general, chimeric mAbs and humanized mAbs minimize the development of human anti-mouse antibody responses. Further, the biological half-life of the chimeric or humanized antibodies in humans is longer than the biological half-life of the parental mouse antibodies. Additionally, the chimeric or humanized antibodies generally change the pharmacokinetics by providing a longer half-life of immunoconjugates containing such antibody, as compared to the half-life of immunoconjugates containing murine antibody.

A chimeric mAb can also be constructed using a standard combination of techniques including polymerase chain reaction (PCR) cloning of antibody variable regions, the use of suitable expression vectors already containing the DNA encoding human constant region, insertion of the DNA for the murine mAb variable region into such vector in forming a recombinant vector, and expression of the resultant chimeric antibody by an expression system containing the recombinant vector (See, e.g., Daugherty et al., 1991, *Nucl. Acids Res.* 19:2471–2476; Maeda et al., 1991, *Human Antibodies and Hybridomas* 2:124–134; herein incorporated by reference). One expression vector can be used in which the vector is constructed so that the variable region and constant region genes are in tandem. Alternatively, the DNA encoding the mouse variable region is inserted into one expression vector, and the DNA encoding the human constant region can be inserted into a second expression vector, followed by transfections using both the first and second expression vectors. Expression systems known to those skilled in the art for production of antibody or antibody fragments include mammalian cells (e.g. cell lines such as COS, NSO, or CHO), phage expression libraries, *Escherichia coli*, and yeast (Adair, 1992, supra).

From the foregoing, it will be obvious to those skilled in the art that various modifications in the above-described methods, and compositions can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the claims are therefore intended to be embraced therein.

What is claimed is:

1. A composition for antiangiogenic therapeutic treatment of an angiogenesis-associated disease comprising tumor angiogenesis or other angiogenesis-associated disease in a mammalian host, wherein the composition comprises a monoclonal antibody, or antigen binding fragments thereof, having binding specificity for crossreactive epitopes shared by endoglin expressed on human vascular endothelial cells and endoglin expressed on murine vascular endothelial cells.

2. The composition for antiangiogenic therapeutic treatment according to claim 1, wherein the fragments are selected from the group consisting of F(ab')$_2$, Fab', Fab, Fv, scFv, Fd', and Fd.

3. The composition for antiangiogenic therapeutic treatment according to claim 1, wherein the antibody is a chimeric antibody comprising a murine variable region having anti-endoglin binding specificity for crossreactive epitopes between human endoglin and murine endoglin, and a human constant region.

4. The composition for antiangiogenic therapeutic treatment according to claim 1, wherein the antibody is a humanized antibody comprising murine hypervariable regions having endoglin binding specificity for crossreactive epitopes shared by human endoglin and murine endoglin, and a constant region and variable region sequences of human immunoglobulin.

5. The composition for antiangiogenic therapeutic treatment according to claim 1, further comprising a pharmaceutically acceptable carrier medium.

6. The composition for antiangiogenic therapeutic treatment according to claim 1, wherein the treatment is of tumor angiogenesis.

7. The composition for antiangiogenic therapeutic treatment according to claim 2, wherein the treatment is of tumor angiogenesis.

8. The composition for antiangiogenic therapeutic treatment according to claim 3, wherein the treatment is of tumor angiogenesis.

9. The composition for antiangiogenic therapeutic treatment according to claim 4, wherein the treatment is of tumor angiogenesis.

10. The composition for antiangiogenic therapeutic treatment according to claim 1, wherein the treatment is of an angiogenesis-associated disease other than tumor.

11. The composition for antiangiogenic therapeutic treatment according to claim 2, wherein the treatment is of an angiogenesis-associated disease other than tumor.

12. The composition for antiangiogenic therapeutic treatment according to claim 3, wherein the treatment is of an angiogenesis-associated disease other than tumor.

13. The composition for antiangiogenic therapeutic treatment according to claim 4, wherein the treatment is of an angiogenesis-associated disease other than tumor.

14. A method for antiangiogenic therapy of tumor in a mammalian host comprising administering a therapeutically effective amount of a composition comprising the monoclonal antibody, or antigen binding fragments thereof according to claim 1.

15. A method for antiangiogenic therapy of tumor in a mammalian host comprising administering a therapeutically effective amount of a composition comprising the monoclonal antibody, or antigen binding fragments thereof according to claim 2.

16. A method for antiangiogenic therapy of tumor in a mammalian host comprising administering a therapeutically effective amount of a composition comprising the monoclonal antibody, or antigen binding fragments thereof according to claim 3.

17. A method for antiangiogenic therapy of tumor in a mammalian host comprising administering a therapeutically effective amount of a composition comprising the monoclonal antibody, or antigen binding fragments thereof according to claim 4.

18. The method for antiangiogenic therapy according to claim 14, further comprising administering a pharmaceutically acceptable carrier medium with the monoclonal antibody, or antigen binding fragments thereof.

19. The method for antiangiogenic therapy according to claim 15, further comprising administering a pharmaceutically acceptable carrier medium with the monoclonal antibody, or antigen binding fragments thereof.

20. The method for antiangiogenic therapy according to claim 16, further comprising administering a pharmaceutically acceptable carrier medium with the monoclonal antibody, or antigen binding fragments thereof.

21. The method for antiangiogenic therapy according to claim 17, further comprising administering a pharmaceutically acceptable carrier medium with the monoclonal antibody, or antigen binding fragments thereof.

22. The method for antiangiogenic therapy according to claim 14, wherein the composition is administered intravenously.

23. The method for antiangiogenic therapy according to claim 15, wherein the composition is administered intravenously.

24. The method for antiangiogenic therapy according to claim 16, wherein the composition is administered intravenously.

25. The method for antiangiogenic therapy according to claim 17, wherein the composition is administered intravenously.

* * * * *